(12) United States Patent
Schoenbach et al.

(10) Patent No.: US 6,326,177 B1
(45) Date of Patent: Dec. 4, 2001

(54) METHOD AND APPARATUS FOR INTRACELLULAR ELECTRO-MANIPULATION

(75) Inventors: Karl H. Schoenbach; Stephen J. Beebe, both of Norfolk; E. Stephen Buescher, Virginia Beach, all of VA (US)

(73) Assignees: Eastern Virginia Medical School of the Medical College of Hampton Roads; Old Dominion University, both of Norfolk, VA (US)

( * ) Notice: Subject to any disclaimer, the term of this patent is extended or adjusted under 35 U.S.C. 154(b) by 0 days.

(21) Appl. No.: 09/546,754

(22) Filed: Apr. 11, 2000

Related U.S. Application Data

(60) Provisional application No. 60/147,099, filed on Aug. 4, 1999.

(51) Int. Cl.$^7$ .................................................... C12N 13/00

(52) U.S. Cl. ........................................... 435/173.7; 600/12

(58) Field of Search ............................. 435/173.7, 173.1, 435/173.4, 173.6; 600/12; 604/20

(56) References Cited

U.S. PATENT DOCUMENTS

| | | |
|---|---|---|
| 4,154,668 | 5/1979 | Zimmermann et al. . |
| 4,429,694 | 2/1984 | McGreevy . |
| 5,019,034 | 5/1991 | Weaver et al. . |
| 5,304,120 | 4/1994 | Crandell et al. . |
| 5,386,837 | 2/1995 | Sterzer . |
| 5,389,069 | 2/1995 | Weaver . |
| 5,464,386 | 11/1995 | Hofmann . |
| 5,527,352 | * 6/1996 | Vona . |
| 5,545,130 | 8/1996 | Hofmann et al. . |
| 5,674,267 | 10/1997 | Mir et al. . |
| 5,688,233 | 11/1997 | Hofmann et al. . |
| 5,702,359 | 12/1997 | Hofmann et al. . |
| 5,776,175 | 7/1998 | Eckhouse et al. . |
| 5,810,762 | 9/1998 | Hofmann . |
| 5,859,327 | 1/1999 | Dev et al. . |
| 5,911,223 | 6/1999 | Weaver et al. . |
| 5,944,710 | 8/1999 | Dev et al. . |
| 5,964,726 | 10/1999 | Korenstein et al. . |
| 5,968,006 | 10/1999 | Hofmann . |
| 5,993,434 | 11/1999 | Dev et al. . |
| 6,009,345 | 12/1999 | Hofmann . |
| 6,014,584 | 1/2000 | Hofman et al. . |
| 6,027,488 | 2/2000 | Hofmann et al. . |
| 6,041,252 | 3/2000 | Walker et al. . |
| 6,043,066 | * 3/2000 | Mangano et al. . |
| 6,068,650 | 5/2000 | Hofmann et al. . |
| 6,120,493 | 9/2000 | Hofmann . |
| 6,135,990 | 10/2000 | Heller et al. . |

OTHER PUBLICATIONS

F. Hofmann et al., "Electric Field Pulses Can Induce Apoptosis", *J. Membrane Biol.*, 169, 103–109 (1999).

H. Hülsheger et al., "Killing of Bacteria with Electric Pulses of High Field Strength", *Radiation and Environmental Biophysics*, 20, 53–65 (1981).

Marshall et al., "Pulse Generator for Biofouling Prevention", Conference Record of the 1998 Twenty–Third International Power Modulator Symposium, IEEE, pp. 52–56 (1998).

Schoenbach et al., "Biological Effects of High Power, Microsecond and Submicrosecond Electrical Pulses," Abstracts from ElectoMed99 Conference, held Apr. 11–Apr. 14, 1999, p. 35.

Schoenbach et al., "The Effect of Pulsed Electrical Fields on Biological Cells", The 1997 11$^{th}$ IEEE International Pulsed Power Conference, Part 1 (of 2), held Jun. 29–Jul. 2, 1997 in Baltimore, MD, IEEE, pp. 73–78 (1997).

Schoenbach et al., "The Effect of Pulsed Electric Fields on Biological Cells: Experiments and Applications", *IEEE Transactions on Plasma Science*, 25, 284–292 (1997).

Schoenbach et al., "Biofouling Prevention with Pulsed Electric Fields", Abstracts from 7$^{th}$ International Zebra Mussel and Aquatic Nuisance Species Conference, held Jan. 28–Jan. 31, 1997 in New Orleans, LA (1997).

Schoenbach et al., "Effect of submicrosecond electric fields on micro–organisms: experiments and applications", *SPIE–Proceedings–Novel Applications of Lasers and Pulsed Power*, 2374, 199–205 (1995).

Stoudt et al., "Demonstration of a Frequency–Agile RF Source Configuration Using Bistable Optically Controlled Semiconductor Switches (BOSS)", *Digest of Technical Papers Tenth IEEE International Pulsed Power Conference held Jul. 3–Jul. 6, 1995 in Albuquerque, NM*, IEEE, pp. 360–365 (1995).

\* cited by examiner

Primary Examiner—Andrew Wang
Assistant Examiner—Konstantina Ketcheves
(74) Attorney, Agent, or Firm—Foley & Lardner

(57) ABSTRACT

A method for intracellular electro-manipulation is provided. The method includes applying at least one ultrashort electric field pulse to target cells. The ultrashort electric field pulse has sufficient amplitude and duration to modify subcellular structures in the target cells and does not exceed the breakdown field of the medium containing the target cells. The amplitude and duration of the ultrashort electric field pulse are typically insufficient to substantially alter permeability of the surface membranes of the target cells, e.g., by irreversibly disrupting the cell surface membranes. An apparatus for intracellular electro-manipulation is also provided. The apparatus includes a pulse generator capable of producing an ultrashort electric pulse output and a delivery system capable of directing the electric pulse output to target cells.

52 Claims, 24 Drawing Sheets

FIG. 7
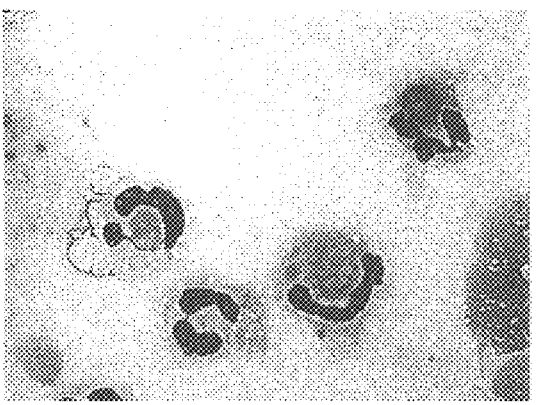
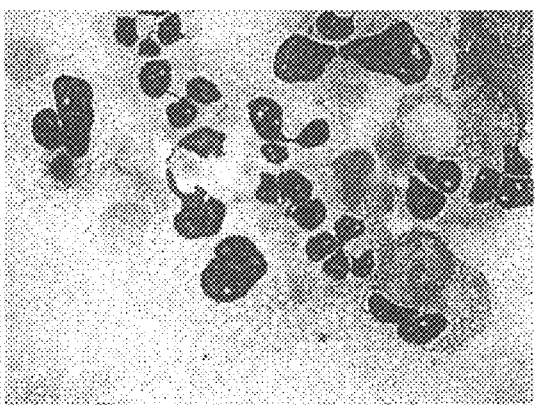
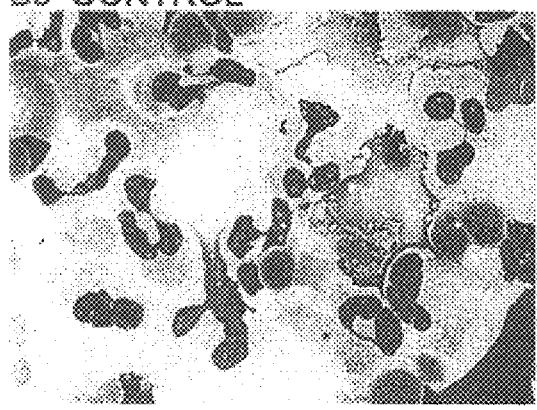
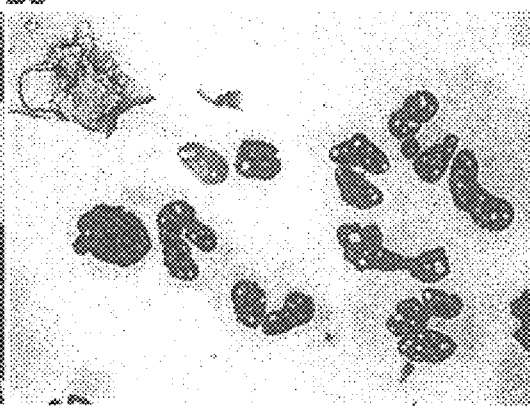

Pulse Width: τ = 60 ns
Voltage: $V_{max}$ = 10 kV
Load: R = 10 Ω → $I_{max}$ = 1 kA
Power: $P_{max}$ = 10 MW
Energy: $En_{max}$ = 0.6 J Energy Density: $W_{max}$ = 6 J/ml
Temperature Increase: $\Delta T_{max}$ = 1.5 K Pulse Width:  τ = 60 ns
Voltage:  $V_{max}$ = 10 kV
Load:  R = 10 Ω → $I_{max}$ = 1 kA
Power:  $P_{max}$ = 10 MW
Energy:  $En_{max}$ = 0.6 J Energy Density:  $W_{max}$ = 6 J/ml
Temperature Increase:  $\Delta T_{max}$ = 1.5 K FIG. 26
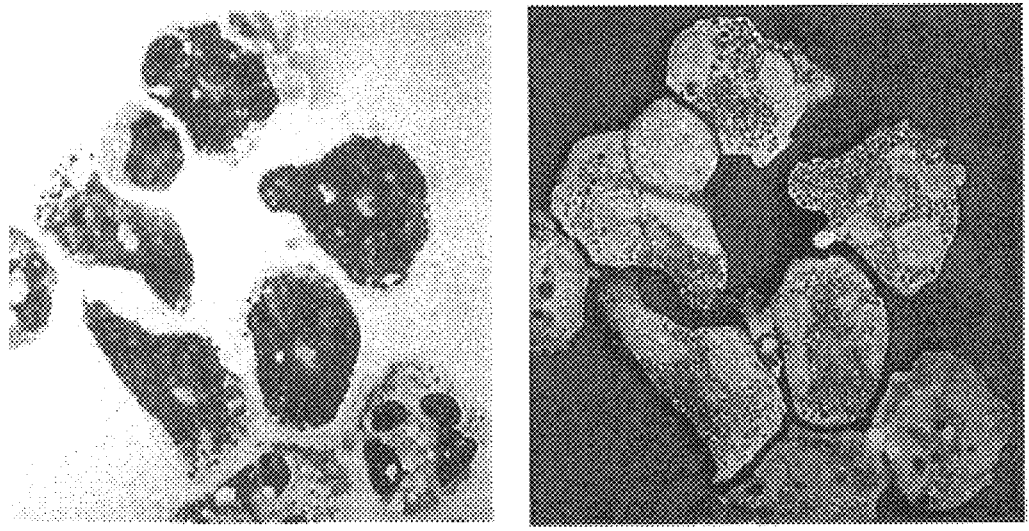
CONTROL
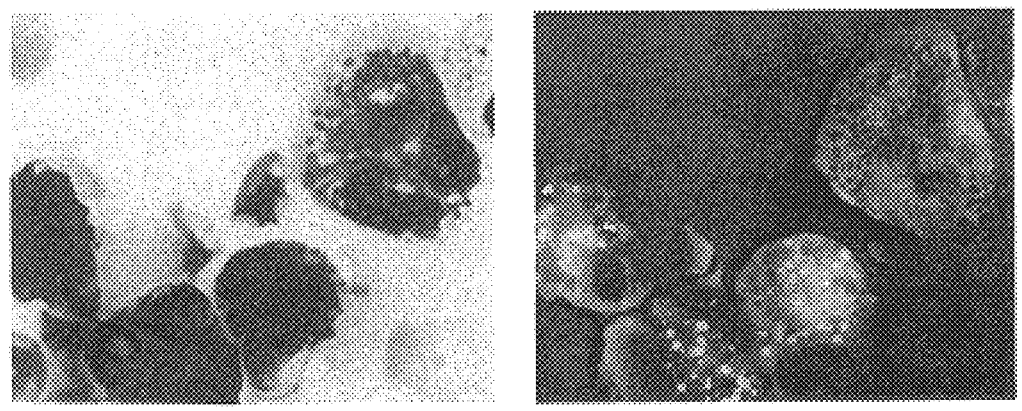
60 ns, 5.3 MV/m x 3
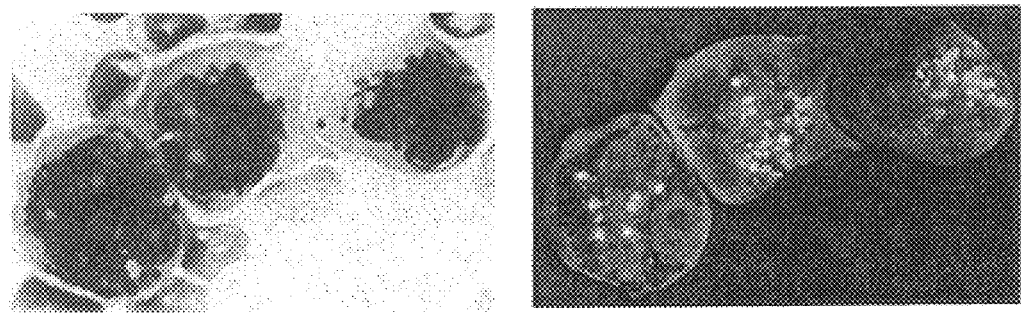
60 ns, 5.3 MV/m x 5

METHOD AND APPARATUS FOR INTRACELLULAR ELECTRO-MANIPULATION

CROSS REFERENCE TO OTHER APPLICATIONS

This application claims priority under 35 U.S.C. §119(e) of U.S. Provisional Application Ser. No. 60/147,099, filed on Aug. 4, 1999, the disclosure of which is herein incorporated by reference.

STATEMENT REGARDING FEDERALLY SPONSORED RESEARCH

The U.S. Government has a paid-up license in the present invention and the right (in limited circumstances) to require the patent owner to license others on terms as provided for by the terms of Grant No. F49620-99-1-00069 awarded by the U.S. Air Force Office of Scientific Research.

BACKGROUND OF THE INVENTION

Biological cells consist of cytoplasm surrounded by a membrane. The cytoplasm is conducting, the membrane, which is made up of a lipid bilayer, can be considered a dielectric. The application of electric fields to biological cells causes buildup of electrical charge at the cell membrane, and consequently a change in voltage across the membrane. For eukaryotic cells the transmembrane voltage under equilibrium condition is approximately 70 mV. In order to affect membrane processes by means of external electric fields, the amplitude of these fields ("E") must be such that it generates a potential difference ("$V_m$") at least on the same order as the resting potential. The amplitude of the electric field is:

$$E = V_m / fa \quad (1)$$

where a is the radius of the cell and f is a form factor which depends on the shape of the cell. For spherical cells, f is 1.5; for cylindrical cells of length l, with hemispheres of diameter d at each end, the form factor is $$f = l/(l - d/3) \quad (2)$$

For a biological cell with an assumed radius of about 5 $\mu$m and a spherical shape, the external electric field required to generate a voltage of the same amplitude as the resting potential across the membrane is on the order of 100 V/cm. Due to their smaller size, the electric field required to affect the membrane permeability of bacteria is much higher, on the order of kV/cm.

For external electric fields of a magnitude such that the change in membrane potential is on the order of the resting potential, voltage induced opening of channels in the membrane causes flux of ions through the membrane. This leads to changes in the ion concentration close to the cell membrane, and consequently causes cell stress. The stress lasts on the order of milliseconds, and generally does not cause permanent cell damage. If the strength of the electric field is increased such that the voltage across the cell membrane reaches levels on the order of one volt, the membrane permeability increases to such a level that either the cell needs from seconds to hours to recover (reversible breakdown), or cell death may occur. The mechanism of the membrane breakdown is not well understood. A common hypothesis is that pores are generated in the membrane. The pores can be of sizes which allow the exchange of macromolecules. If the transmembrane voltages are sufficiently high the pores will not close anymore. The use of the reversible breakdown effect has been reported in electroporation and in biofouling prevention. The irreversible effect has been employed in the debacterialization of water and food.

The effect of electric fields on biological cells is not simply dependent on the magnitude of the applied electric field, but also on its duration. This can be understood by considering a model for the electrical equivalent circuit of the cell, shown schematically in FIG. 1. The model shown in FIG. 1 does not take the effect of structures inside the cell into account. The cell (in suspension) is modeled by a resistance and capacitance. For a pulse duration which is long compared to the dielectric relaxation time of the suspension, the capacitive component of the suspension impedance can be neglected. For many cell suspensions and seawater (i.e., aqueous solutions with relatively high ionic strengths) the dielectric relaxation time is on the order of nanoseconds. The cell membrane can be modeled as capacitor, the cytoplasm as a resistor. The outer membrane contains channels which are affected by the applied voltage and allow flow of ions through the membrane, representing a leakage current. The voltage-gated channels can be modeled as variable, voltage-dependent resistors.

When a voltage pulse is applied to the cell, charges accumulate at the membrane and the membrane voltage is increased. The charging time constant of the cell membrane may be represented by equation (3):

$$\tau = (\rho_1/2 + \rho_2) Cr \quad (3)$$

with $\rho_1$ being the resistivity of the suspending medium, e.g. water, $\rho_2$ being the resistivity of the cytoplasm, C the capacitance per unit area, and r the cell radius (spherical cell). Using typical data for cells, the duration of the electric field pulses required to generate a potential difference of 1 V across the membrane can be calculated. The energy, W, dissipated in the suspension is given by:

$$W = E^2 \tau / \rho_1 \quad (4)$$

Electric field and energy density are plotted in FIG. 2 versus pulse duration for spherical cells of radius 5 $\mu$m in a suspension with a resistivity of 50 $\Omega$cm. The resistivity of the cytoplasm is assumed to be 100 $\Omega$cm. The curves show a minimum at 100 nsec. This is the pulse duration where the stunning or killing of these kind of biological cells is predicted to be most effective. Experimental studies have reported which confirm the presence of such a minimum.

Modifications of cells which lead to rupture of the cell membrane can lead to cell death via necrosis, a nonphysiological type of cell destruction. It would be advantageous to be able to initiate cell death via apoptosis in a selective manner. This would allow the destruction of cells without engendering the non-specific damage to surrounding tissues due to inflammation and scarring that is normally observed with necrosis. The ability to selectively modify cells in ways that lead to apoptosis could provide a new method for the selective destruction of undesired cells/tissue (e.g., cancer cells, fat cells or cartilage cells) while minimizing side effects on surrounding tissue.

SUMMARY OF THE INVENTION

The present invention relates to a method for modifying cells by intracellular electro-manipulation. The method includes applying one or more ultrashort electric field pulses to target cells. The ultrashort electric field pulse generally has at least a sufficient amplitude and duration when applied as a sequence of pulses to modify subcellular structures in the target cells. The amplitude of individual pulses do not exceed the irreversible breakdown field of the target cells. The amplitude and duration of the ultrashort electric field pulse(s) are typically chosen so as to be insufficient to permanently alter permeability of surface membranes of the target cells, e.g., by rupturing the surface membranes.

The targeting of substructures of cells rather than cell membranes can have a utility in treatments involving the selective destruction of cells (e.g., tumor cells) without substantially damaging surrounding tissue(s). Most therapeutic applications of the pulsed electric field method require that the fields be applied to tissues rather than single cells. With the comparatively long pulses currently employed in such treatments (e.g., several hundred microseconds in length), however, the electric field seems to be less effective in treating tissue compared to single cells. It is known that although generalized tissue can be regarded as an aggregate of cells, with different types of cell-cell interconnections, tissue electroporation consists of electroporation of individual cells. There are two major differences between the electroporation of individual cells in a suspension and the electroporation of tissue. In tissue, the local extracellular electric field depends in a complicated way on the many neighboring cells. In addition, for tissues the ratio of the extra- to intracellular volume is usually small, just the opposite of most in vitro electroporation conditions. This means that if chemical exchange between the intra- and extracellular volumes is the main cause of cell stress, and therefore cell death, tissue electroporation with microsecond pulses may be intrinsically less damaging than most in vitro electroporation conditions. Since ultrashort pulses affect the interior of the cell, such pulses are expected to have roughly the same effect on tissues as on individual cells.

Another advantage of using ultrashort pulses of the type employed in the present method is the low energy of these pulses. Although the electrical power of the pulses may be many megawatts, the energy of these pulses is often so low (due to their short duration) that any thermal effects on cells can be neglected. The present pulse power method is thus a "cold" method which can allow modification of cells via electrical effects without creating any substantial related thermal effects. For example, the thermal effects associated with the pulses employed in the present method typically only generate temperature increases in the bulk medium or tissue on the order of 1–2° C. The ability to electrically modify cells in a "cold" manner is particularly useful where the intent is to selectively modify subcellular structures within a target cell without substantially effecting the cell membrane.

The present invention also provides an apparatus for intracellular electro-manipulation. The apparatus includes a pulse generator capable of producing an ultrashort electric pulse output and a delivery system capable of directing the electric pulse output to target cells.

BRIEF DESCRIPTION OF THE DRAWINGS

FIG. 7 shows microscopic examinations (160× magnification) of stained human neutrophils immediately after being subjected to a 60 nsec, 6 kV electric field pulse ("A42"), 300 nsec, 4 kV electric field pulse ("B6"), or 300 nsec, 6 kV electric field pulse ("B8").

FIG. 26 shows microscopic examination of the effects of Triton X-100 treatment on free calcein staining of eosinophil granules; UPPER ROW: Wright-Giemsa stained (above) and fluorescent (below) images of calcein-AM (1 μM) stained eosinophils (left), eosinophils incubated (5 minutes) in 0.001% Triton X-100+1 μM free calcein (center) and eosinophils incubated in 0.005% Triton X-100+1 μM free calcein for 5 minutes;
BOTTOM ROW: Wright-Giemsa stained (above) and fluorescent (below) images of eosinophils treated with 1 μM free calcein+0.005% Triton X-100 for 5 minutes (left), eosinophils treated with 0.01% Triton X-100+1 μM free calcein (5 minutes) (center) and eosinophils incubated in 0.05% Triton X-100+1 μM free calcein for 5 minutes.

DETAILED DESCRIPTION

Figure 1:
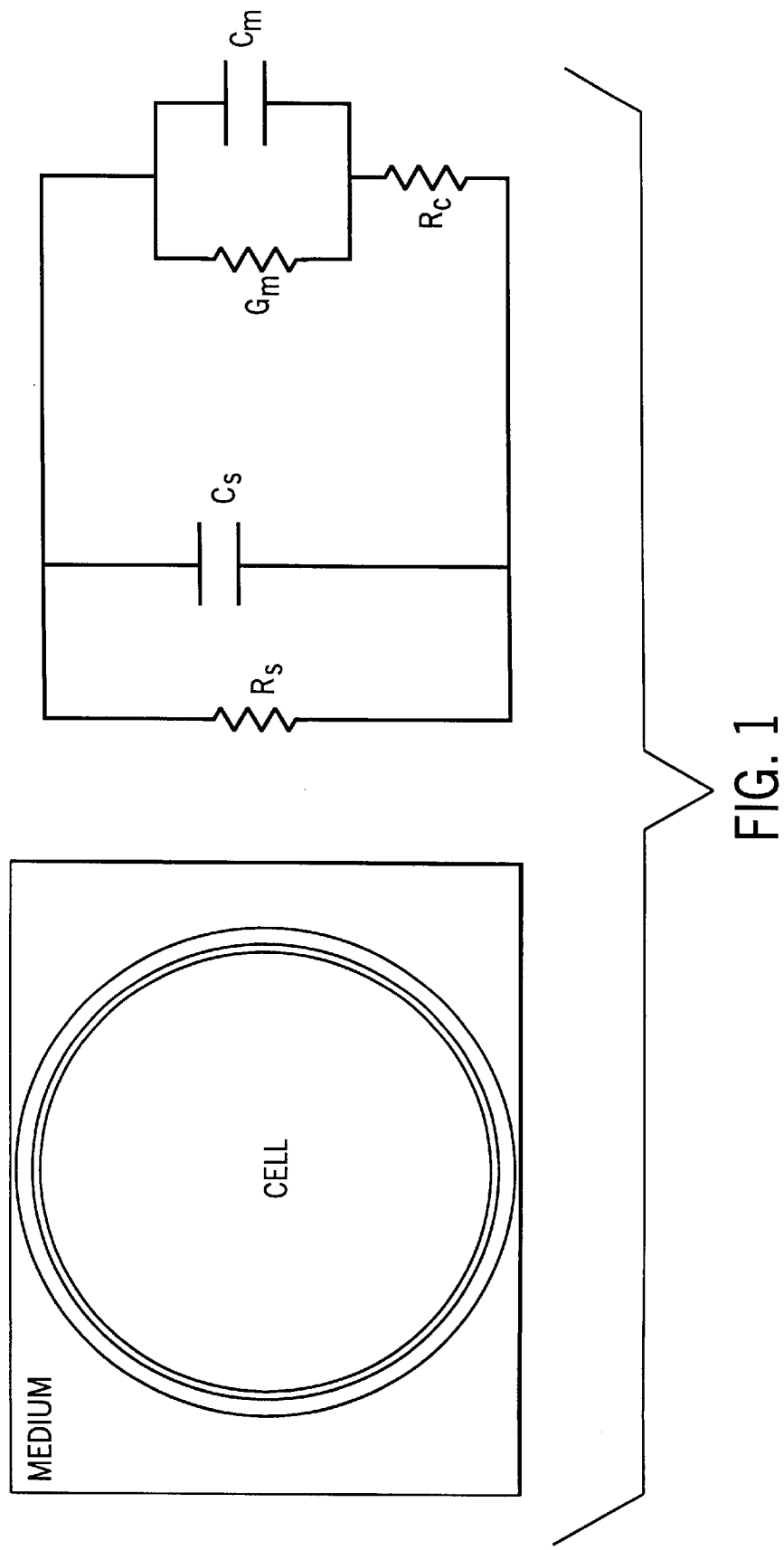
FIG. 1 depicts an electrical equivalent circuit of a cell in suspension.
Figure 2:
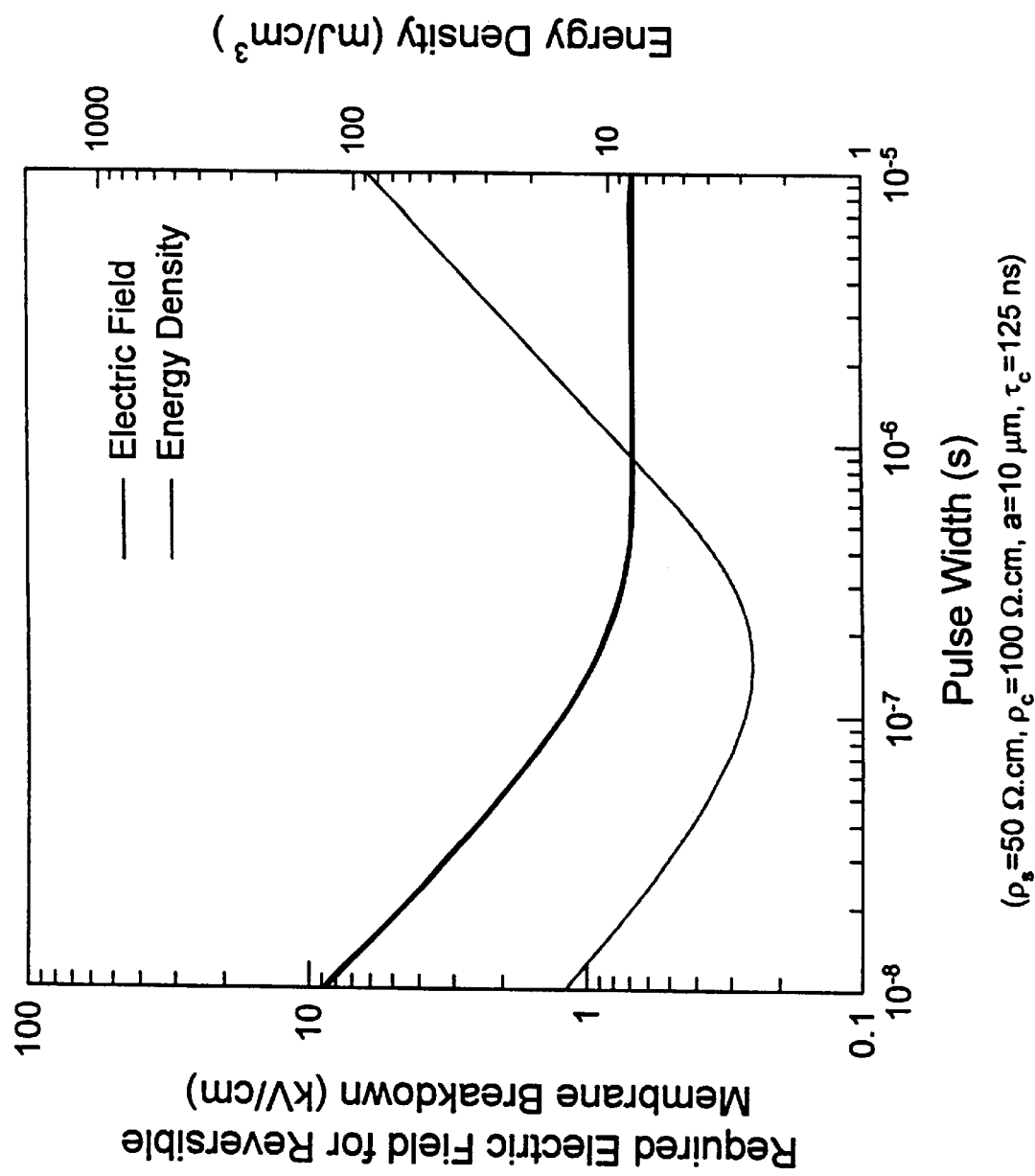
FIG. 2 is a graph showing the electric field required to charge a cell surface membrane to 1 V and corresponding energy density versus pulse duration.
Figure 3:
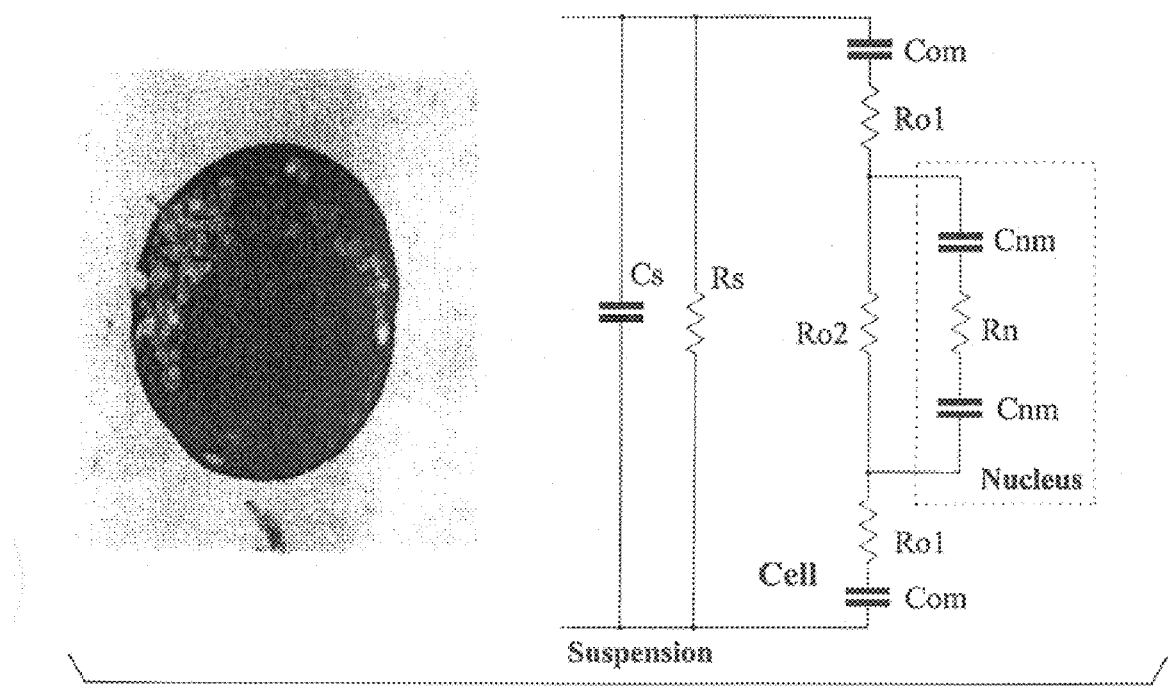
FIG. 3 shows an HL-60 leukemia cell and a simplified electrical equivalent circuit of a cell containing a nucleus.

In the simple equivalent circuit shown in FIG. 1, the cell was modeled as a homogeneous, conductive medium surrounded by a dielectric membrane. Taking substructures in cells into account, such as the cell nucleus in eukaryotic cells, requires a more complex model of the equivalent circuit. HL-60 Leukemia cells can be used to demonstrate the complexity of structures inside the cell. The nucleus is clearly visible as are smaller substructures within it, e.g., nucleoli. The substructures can be modeled by treating the membrane surrounding the nucleus as a capacitor and the interior of the nucleus as a resistor, both elements in series and in parallel to the resistance which describes the cytoplasm in the first, simplified, equivalent circuit (see, e.g., FIG. 3). Similarly, the nucleoli can also be described by an additional capacitor resistor arrangement in parallel to the nucleus resistance.

Basic electrical circuit principles indicate that low frequency electric fields will affect mainly the larger capacitance, that is the outer membrane. With increasing frequency, the outer membrane, however, will be effectively shorted out, and the applied voltage will appear across the inner (nucleus) membrane. This model predicts that at frequencies around 1 MHz, the applied voltage should appear mainly across the membrane of the nucleus, rather than across the outer membrane. This means that shorter pulses with higher frequency components would be expected to affect the nucleus of a cell rather than the cell membrane.

Assuming that the diameter of target intracellular structures, d, is small compared to the cell diameter, and that the structures are located in the center of the cell, the voltage across the intracellular structure, $V_{is}$, can be modeled according to the equation:

$$V_{is}=E(t)d=j(t)dp_{is}=dp_{is}(E(t)/p_c)\exp(-t/T_c) \quad (5)$$

where $p_{is}$ is the resistivity of the target intracellular structure. The charging of the intracellular membrane is predicted to occur with a time constant, $T_{is}$:

$$T_{is}=c_{is}d/2(p_c/2+p_{is}) \quad (6)$$

The voltage across the intracellular structure membrane, $V_{ism}$, is consequently given as:

$$V_{ism}=V_{is}(1-\exp{-t/T_{is}})=dp_{is}(E_0/p_c)\exp(-t/T_c)(1-\exp(-t/T_{is}))[u(0)-u(T)] \quad (7)$$

Figure 4:
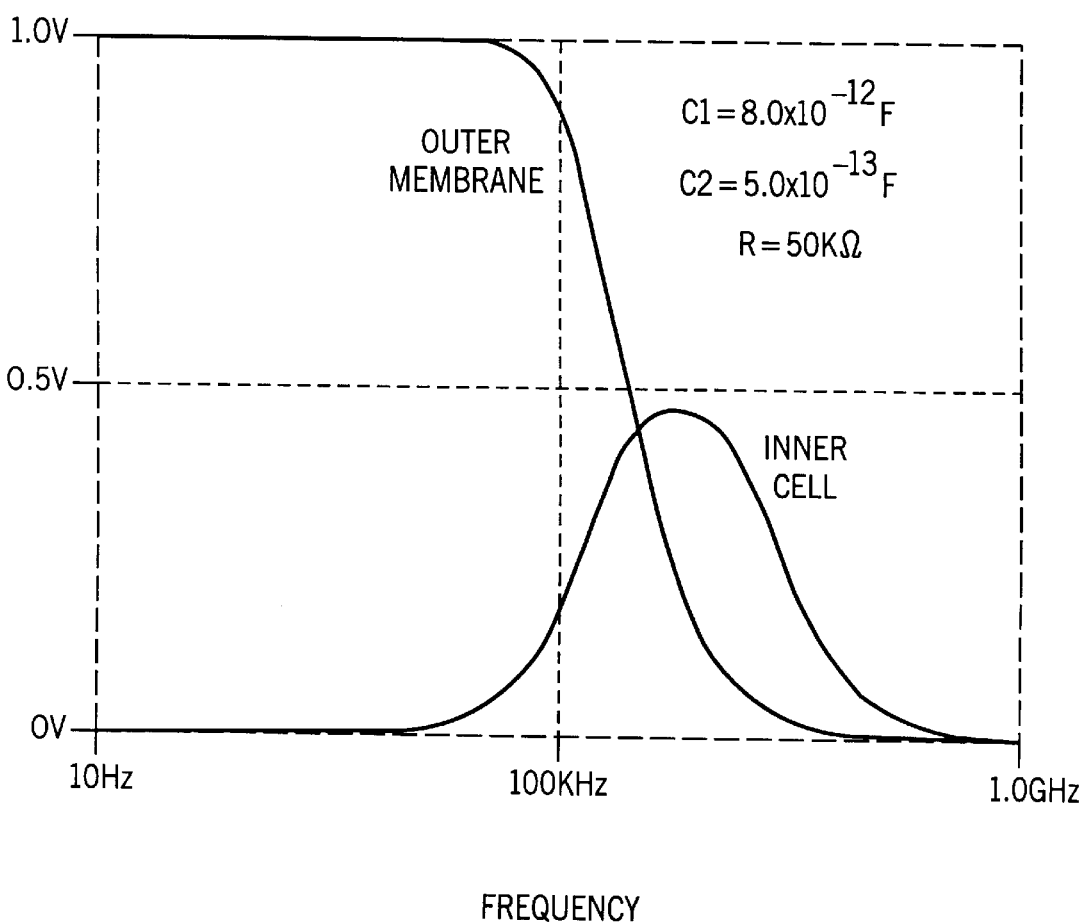
FIG. 4 shows voltage-time curve for modeling of application of 60 nsec and 6 $\mu$sec electric field pulses to a theoretical cell. The dotted line shows the applied voltage pulse, the dashed line shows calculated voltage across the surface membrane, the heavy solid line shows the voltage across intracellular membranes.

The temporal development of the applied voltage, the voltage across the surface membrane and that across the intracellular structure membrane (equ. 7) is shown in FIG. 4 for the cellular parameters D=0 μm, d=5 μm, $p_c=p_n=100$ Ωcm, $c_m=1$ μF/cm², $c_n=0.5$ μF/cm², and a pulse duration of T=60 nsec. In this instance, a rectangular pulse is applied, while in experimental situations, the pulse is more typically trapezoidal. The value for the capacitance of the outer cell surface membrane has been reported in published work (see, e.g., Schwan, *Biophysik*, 1, 190 (1963)) and the capacitance of intracellular structures is assumed to be either the same or half of this value, depending on the structure of the specific intracellular membrane. The nucleus is surrounded by two lipid bilayer membranes that make up the nuclear envelope, whereas other intracellular structures (e.g., intracellular granules) may have only one lipid bilayer membrane surrounding them.

From this simple theoretical model, a number of conclusions can be drawn:

1. The voltage across the intracellular membrane may reach values on the same order as the voltage across the outer membrane if the pulse duration is larger than the charging time of the intracellular membrane and the pulse rise time is small compared to this charging time. The importance of the second condition can be illustrated by considering the electrical response of a cell to two pulses with the same electric field, but quite different rise times (and durations). The electrical pulses are presumed to be similar in shape but the ultra-short (60 nsec) duration pulse has rise and fall times of 10 nsec, while the longer pulse (6 μsec) has rise and fall times of 1 μsec. If the cell dimensions, capacitances and resistivities are the same, the short, fast rise-time pulse results in voltages across the intracellular and surface membranes that are comparable for both membranes, while the longer pulse with the microsecond rise-time results in almost negligible voltage across intracellular membrane. The voltage across the outer membrane for the longer pulse, however, reaches the value of the applied voltage, favoring electroporation of this membrane. This effect has been used in medical applications where pulses in the temporal range of tens of microseconds to milliseconds are used to facilitate drug and gene delivery into cells.

2. To reach voltages in excess of 1 volt across intracellular membranes, electric field amplitudes in the megavolt/m range are required on a time scale of the charging time of the intracellular membrane. For intracellular structures with characteristic dimensions of $\mu$m, membrane capacitances on the order of $\mu F/cm^2$, and cytoplasm resistivities of 100 $\Omega$cm, the charging time (equ. 6) is less than 10 nsec. The required rate of change of the electric field intensity is consequently $dE/dt > 10^{14}$ volt/(meter second). Only if both conditions are satisfied (i.e., large electric field amplitude plus extremely fast rates of change in the electric field), can intracellular effects be expected.

3. The voltage across intracellular membranes is expected to be almost linearly dependent on the diameter of the intracellular structure. Stronger effects at larger internal structures would therefore be expected with the same electrical parameters.

Reaching a critical voltage across the intracellular membrane is a necessary but not sufficient condition for "intracellular electromanipulation" ("IEM"). In order to change the structure of the membrane, e.g., open membrane defects to a size that allows passage of macromolecules through them, the critical voltage needs to be applied long enough to allow expansion of the defects to appropriate size. Estimates of the voltage required to achieve such effects at the surface membrane have been reported, but no such estimates exist for intracellular membranes. The model described here is therefore only providing necessary conditions for the onset of electric field dependent effects on intracellular membranes, and does not describe the specific processes occurring within the membranes. Nonetheless, this analysis clearly illustrates that reducing the pulse duration, or more precisely, reducing the pulse rise time to values less than the charging time for intracellular membranes, and increasing electric field intensities to megavolt/m range should allow preferential targeting of intracellular membranes. The experimental work described herein establishes that at least in certain cases, the application of a sequence of multiple ultrashort pulses within a relatively short time period can amplify the effect on intracellular substructures without causing substantial defects in the outer surface membrane.

The present method typically employs ultrashort electric field pulses having sufficient amplitude and duration to modify subcellular structures in the target cells, at least when applied as a sequence of ultrashort pulses within a relatively short time period, e.g., a sequence of 3–5 ultrashort pulses within a time interval of 10 seconds or less. The amplitude and duration of each ultrashort electric field pulse can be chosen so that it is insufficient to alter permeability of surface membranes of the target cells, e.g., by inducing pores in the cell membranes. The target cells are generally either in suspension in solution or present as part of a tissue. Each ultrashort electric field pulses typically has a pulse duration of no more than about 1 microsecond and an amplitude of at least about 20 kV/cm. Characterized in a different fashion, the ultrashort electric field pulses typically have a pulse duration of no more than about 1 microsecond and a total energy of at least about 75 mJ/cc. Preferably, the ultrashort electric field pulses have a total energy of no more than about 10 J/cc. More typically, total energy of each ultrashort electric field pulse is about 75 mJ/cc to about 2,000 mJ/cc and, preferably, about 100 mJ/cc to about 1,000 mJ/cc. In instances where extremely short pulses are applied, e.g., pulses having a duration of about 10 nanoseconds or less, the total energy of the electric field pulse may only be on the order of about 10 to 20 mJ/cc. In addition to having short durations, the electric field pulses used in the present methods commonly have rise times of 50 nsec or less.

The amplitude of an electric field (the applied voltage divided by distance between electrodes) pulse is generally at least about 20 kV/cm, but should not exceed the breakdown field of the suspension or tissue which includes the target cells. The breakdown field increases with decreasing pulse duration, and can be experimentally determined. Under the conditions commonly employed in the present method, however, the breakdown field does generally not exceed 500 kV/cm. Electric field pulses employed in the present methods which have durations of 10 to 500 nsec typically have amplitudes of about 20 kV/cm to about 300 kV/cm.

To minimize the potential effects on the bulk temperature of the medium ("thermal effects"), the electrical field pulses generally have a rapid rise time and short duration. The pulses should preferably be less than one microsecond, but more than 100 picoseconds in duration. A common pulse duration is about 1 nanosecond to about 500 nanoseconds, with pulses typically having a duration of about 10 to a 300 nanoseconds. The optimum pulse duration will vary depending on the cell type, tissue type and desired treatment, among other factors. The pulse should be preferentially rectangular or trapezoidal, but other pulse shapes may also used. For example, in order to open both the outer and inner cell membranes, an intense short pulse might be combined with a less intense longer pulse. Other examples of suitable pulse shapes include exponential decaying pulses, unipolar pulses and bipolar pulses.

The rise time of the ultrashort electric field pulse is typically no more than about 20% and, preferably, no more than about 10% of the pulse duration. For example, if the pulse duration is about 100 nanoseconds, the rise time of the pulse is preferably about 10 nanoseconds or shorter. For pulses with pulse durations of about 400 nanoseconds or longer, the pulse rise times of about 30–40 nanoseconds are common. With pulses having extremely short durations, e.g., one nanosecond or less, the rise time is often a greater percentage of the pulse duration. For example, pulses with a duration of less than one nanosecond, can commonly have a rise time which is up to about 50% of the pulse duration.

Figure 24:
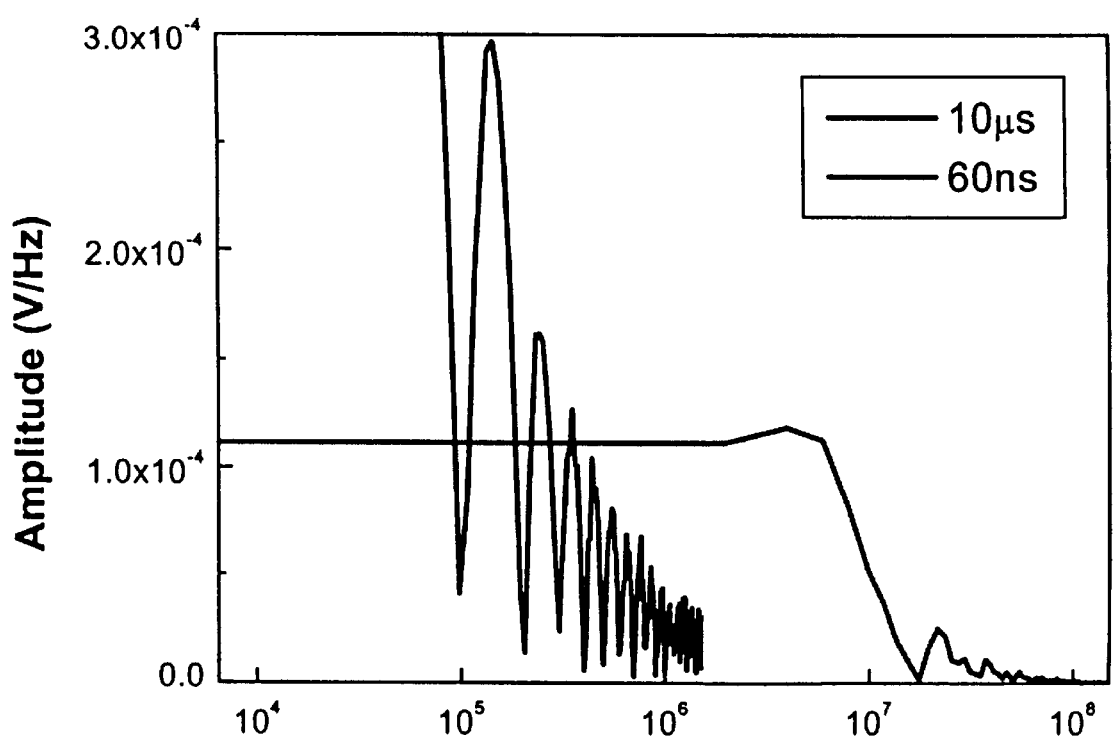
FIG. 24 is a graph depicting the Fourier spectrum (as a plot of amplitude in V/Hz versus frequency) for the 60 nsec and 10 μsec pulses shown in FIG. 23.

The duration, rise time and the frequency distribution of the Fourier transform of the pulse are related. FIG. 24 shows the Fourier spectrum of a short pulse (60 nsec) which extends to the 10 MHz range and for a long pulse (10 microsec) which extends up to the 100 KHz range. With increasing frequency (i.e., decreasing pulse rise time), the outer surface membrane of the target will be effectively shorted out, and the applied voltage will appear across the inner (nucleus) membrane. This behavior is shown in FIG. 4, where the voltage across the surface (outer) membrane and that across the nucleus membrane is plotted versus frequency. FIG. 4 predicts that at frequencies around 1 MHz, the applied voltage should appear mainly across the membrane of subcellular structures, such as the nucleus, rather than across the outer surface membrane. Electric field pulses with duration of less than about 1 microsecond and rise times of 40 nanoseconds or less have Fourier transforms which include frequencies above 1 MHz with substantial amplitudes.

Figure 21:
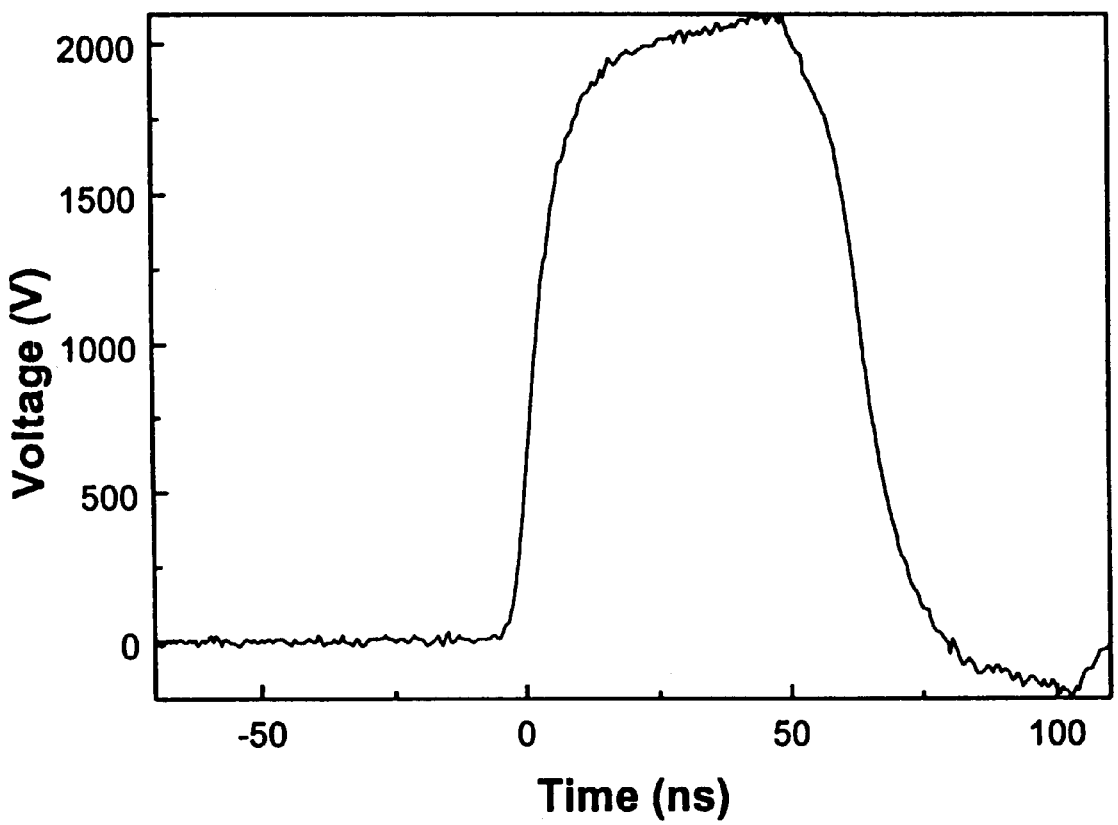
FIG. 21 is a graph depicting its shape of an exemplary electric field pulse (as a plot of voltage versus time) which can be employed in the present methods.
Figure 23:
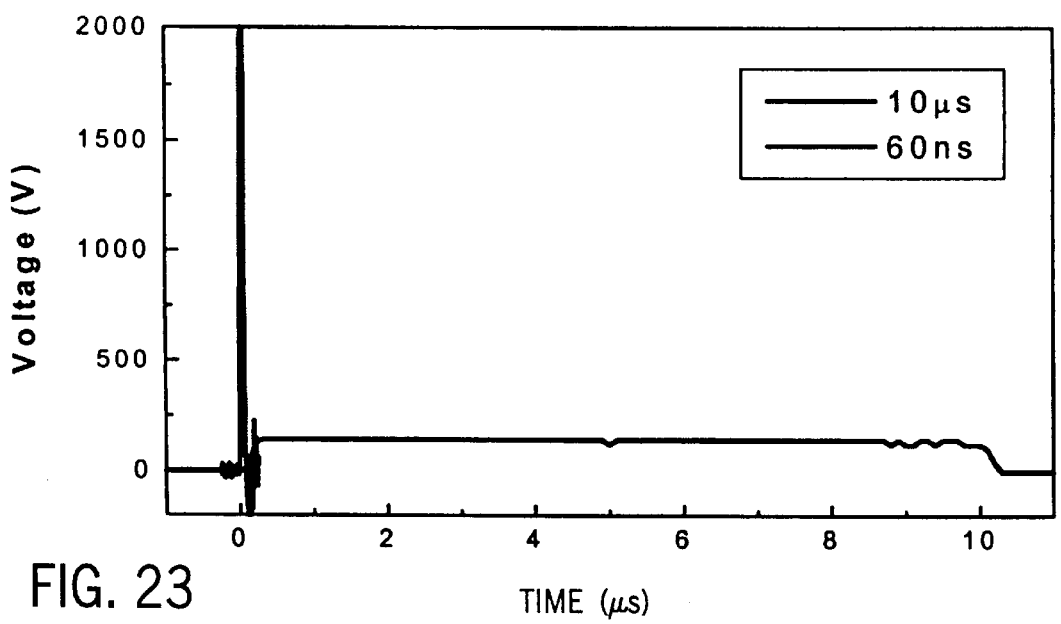
FIG. 23 is a graph (voltage versus time) depicting the shape of an exemplary 60 nsec pulse in comparison to a 10 microsecond (10 μsec) pulse.

The Fourier spectrum of the pulses which are employed in the present methods can include frequencies with substantial amplitudes up to about 1 GHz. Typically, the pulses employed in the present methods have Fourier spectra which include frequencies above 1 MHz with amplitudes greater than 50% of the maximum voltage in the spectrum (referred to hereinafter as greater than "$V_{MAX}/2$"). Preferably, the Fourier spectra of the pulses includes frequencies between 5 to 50 MHz with amplitude greater than $V_{MAX}/2$. For example, a 60 nanosecond rectangular pulse such as depicted in FIG. 21 has a Fourier spectrum which includes frequencies with amplitude greater than $V_{MAX}/2$ up to about 10 MHz. In contrast, the Fourier spectrum of a 10 microsecond rectangular pulse only has frequencies of this amplitude up to about 200–500 kHz (see comparison in FIGS. 23 and 24).

As indicated above, to modify subcellular structures in target cells it may be advantageous to apply a series of ultrashort electric field pulses within a relatively short time interval. For example, it has been found that the application of a sequence of 3 to 5 ultrashort electric field pulses (e.g., trapezoidal pulses with durations of 10–300 nsec and amplitudes of about 25 to 300 kV/cm) may be more effective at modifying intracellular substructures than a single pulse of the same amplitude and duration (see Example 9). For example, the application of a multipulse sequence with a roughly one second interval (delay) between pulses can rupture granules within eosinophils without significant damage to the outer cell membrane. Where multipulse sequences are employed in the present methods, the time interval between subsequent pulses may vary over a wide range, e.g., between 1.0 millisecond and 100 seconds. As another example, multiple pulse sequences with time interval between pulses of about 0.1–3 seconds are quite suitable for initiating apoptosis. Although larger numbers of pulses may be employed, the multipulse sequences utilized in the present methods typically include up to about 20 pulses, which are generally spaced at regular time intervals. Suitable results can often be obtained for certain types of cells (e.g., eosinophils, neutrophils and T-lymphocytes) by applying 3–5 ultrashort electric field pulses within a relatively short time period, e.g., within a time period no longer than about 5 to 10 seconds. As indicated above, the amplitude and duration of the ultrashort electric field pulse are typically chosen so that the sequence of pulses does not permanently alter permeability of surface membranes of the target cells, e.g., by rupturing the surface membranes.

The present method may be used to modify a variety of cells, For example, the target cells may be any of a variety of common cells, such as fat cells, bone cells, vascular cells, muscle cells, cartilage cells and the like. In some instances, the technique may be used to selectively modify certain types of cells in the presence of other cells. For example, the parameters of the present method may be adjusted to selectively induce apoptosis in cancer cells (e.g., leukemia cells) without substantially affecting normal cells in surrounding tissue. As another example, the technique may be utilized to selectively destroy eosinophils in a mixture including eosinophils and neutrophils (see, e.g., Table II in Example 4 herein). The experiments described herein indicate that the present techniques may be used to selectively modify faster growing cells in the presence of slower growing cells (e.g., cells in stationary phase). In other instances, the selectivity may be simply based on spacially limiting the application of the ultrashort electric field pulse(s). For example, by using an appropriate configuration of electrodes, cells within a predetermined area of tissue may be selectively modified in vivo (e.g., through initiation of apoptosis) without altering cells in the immediately surrounding tissue. Devices which incorporate such electrode configuration are currently employed with conventional electroporation pulses (pulses with $\mu$sec duration) to enhance the delivery of therapeutic drugs to cells within a predetermined area.

In one embodiment, the present method can be used to modulate cell function, either through enhancing or attenuating the particular cell function depending on the cell type, phase of the cell and intended treatment. For example, target cells can be subjected to an electric field pulse of sufficient amplitude and duration to modify chemotactic activity in the target cells without reversibly disrupting the permeability of surface membranes in the target cells. Under appropriate conditions, e.g., by applying electric field pulses of 60 to 300 nsec duration having total energies of about 150 to 1000 mJ/cc, the chemotactic activity of cells,such as human neutrophils, can be inhibited (see, e.g., Example 5).

In another embodiment, this application provides a method that can be used to initiate apoptosis in target cells by applying at least one ultrashort electric field pulse with a pulse duration of no more than about 1 microsecond to the target cells. In such instances, electric field pulse commonly has a total energy of at least about 75 mJ/cc, although pulses with lower energies may be employed, in particular where the pulse has an extremely short duration and a relatively high amplitude or where sequences of multiple pulses are applied to the target cells within a relatively short time interval, e.g., with a spacing of 1–2 seconds between succeeding pulses.

Upon choice of the correct parameters, the present method can be employed to selectively destroying target cells in a mixture including the target cells and a second type of cells. For example, the method can be used to selectively destroy eosinophils in a mixture including eosinophils and neutrophils.

In yet another embodiment, present application provides a method of enhancing the proliferation of target cells in a non-proliferative state. This method includes applying at least one ultrashort electric field pulse of sufficient amplitude and duration to modify the target cells without irreversible disruption of cell surface membranes in the target cells. Depending on the particular cell type and phase of cell growth, the enhancement of proliferation may be induced be application of an electric field pulse of no more than 1 microsecond in duration and having an amplitude and/or total energy as low as 10 kV/cm and 10 mJ/cc, respectively. When the inducement of enhanced cell proliferation is the objective, the amplitude, duration, rise time and number of the ultrashort electric field pulse(s) are generally chosen so as to avoid the initiation of apoptosis in a substantial fraction of the target cells.

Intracellular Electro-Manipulation Apparatus

Figure 20:
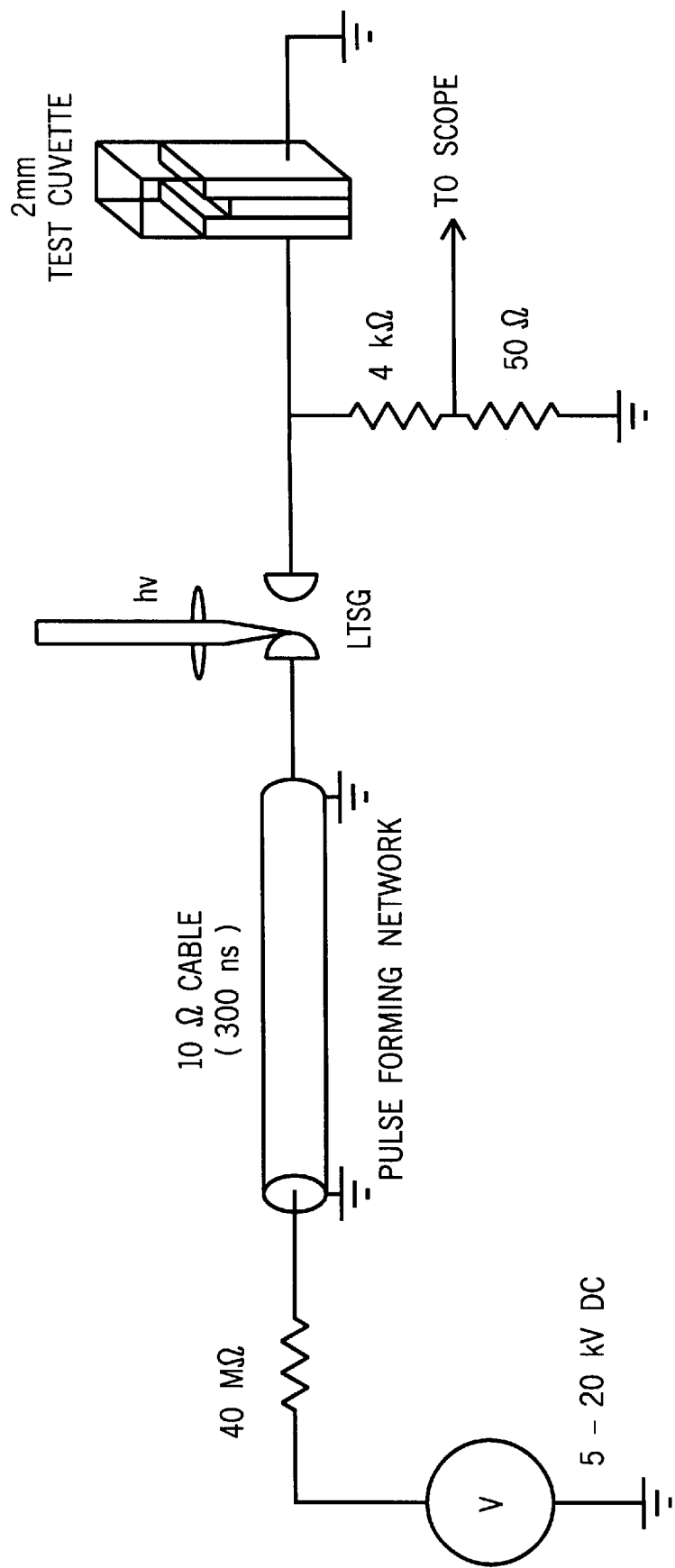
FIG. 20 depicts a schematic of an apparatus for modifying cells which includes a line type pulse generator with a laser triggered spark gap switch.
Figure 22:
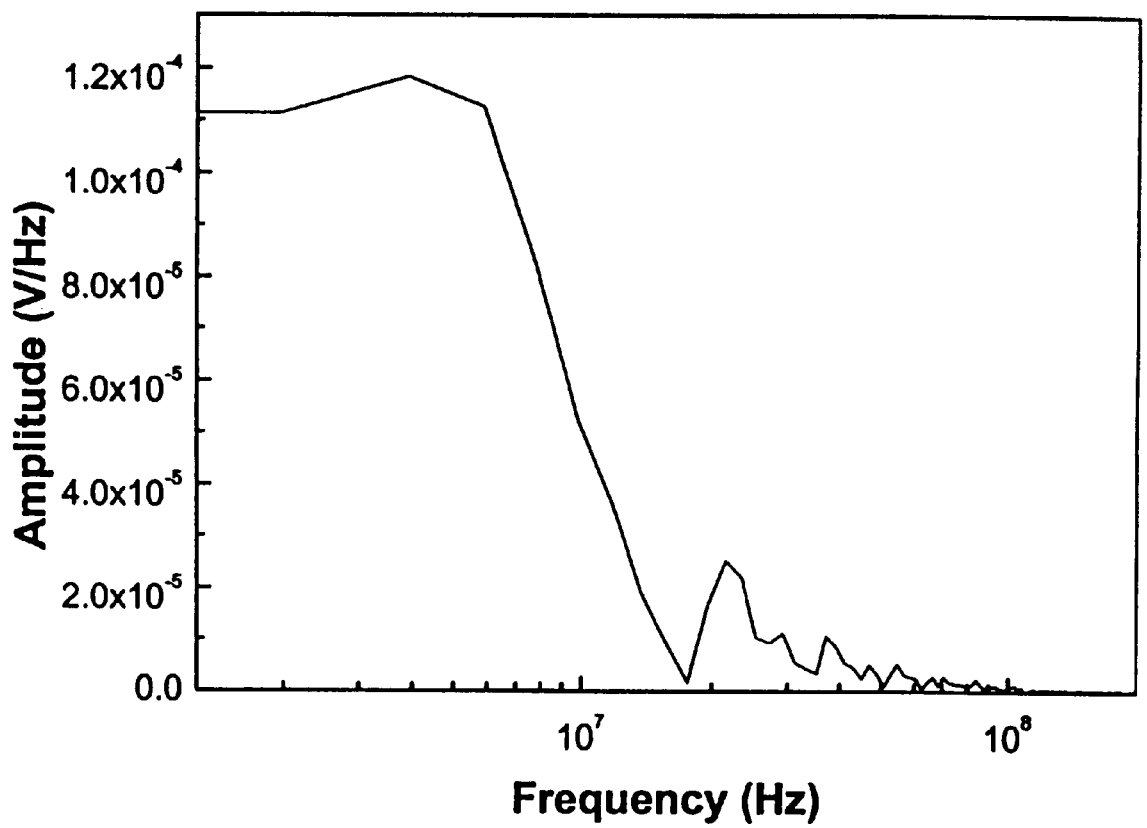
FIG. 22 is a graph showing the Fourier spectrum (as a plot of amplitude in V/Hz versus frequency) of the electric field pulse shown in FIG. 21.

The present method typically employs an apparatus for intracellular electro-manipulation which includes a pulse generator and a delivery system adapted to direct the electric pulse output to target cells. The pulse generator includes a pulse forming network and a high voltage switch. The pulse forming network may be a high voltage cable, a strip-line, or a pulse forming network constructed of individual capacitors and inductors in a transmission line arrangement. The high voltage switch can suitably be a gaseous, liquid or solid state switch. The energy in the pulse forming network may be stored capacitively, which requires a closing switch to release a pulse, or inductively, which requires an opening switch to release a pulse. Upon triggering of the switch, an electrical pulse is launched into the load, i.e., the target cells in suspension or tissue form. The switch can be triggered by a variety of common methods, e.g., optically or electrically. The latter can b accomplished by employing a third electrode or by overvolting the switch. An example of a suitable cable pulsed power system, designed to generate ultrashort pulses of the type employed in the present method is shown in FIG. 20. FIG. 21 shows a typical shape of a pulse employed in the present methods and the corresponding Fourier spectrum of the pulse is shown in FIG. 22. The electrical field pulses can be varied in length ("duration") by changing the pulse forming network, such as by reducing or increasing the length of the cable or stripline, or by using a switch which can be closed and opened. One specific example of an apparatus suitable for modifing cells by intracellular electro-manipulation is described in Example 10 herein.

The "load," which includes the target cells in tissue or suspended in a medium, is placed between two or more electrodes. These electrodes may be solid material (in any of a number of suitable shapes, e.g., planar, cylindrical, spherical, etc), wires or meshes or combinations thereof. One (set of) electrode(s) is connected to the high voltage connection of the pulse generator, and a second (set of) electrode(s) is connected to the ground connection of the pulse generator in a suitable manner, e.g., via a second stripline or high voltage cable. The electrode material is a conductor, most commonly metal.

Figure 25:
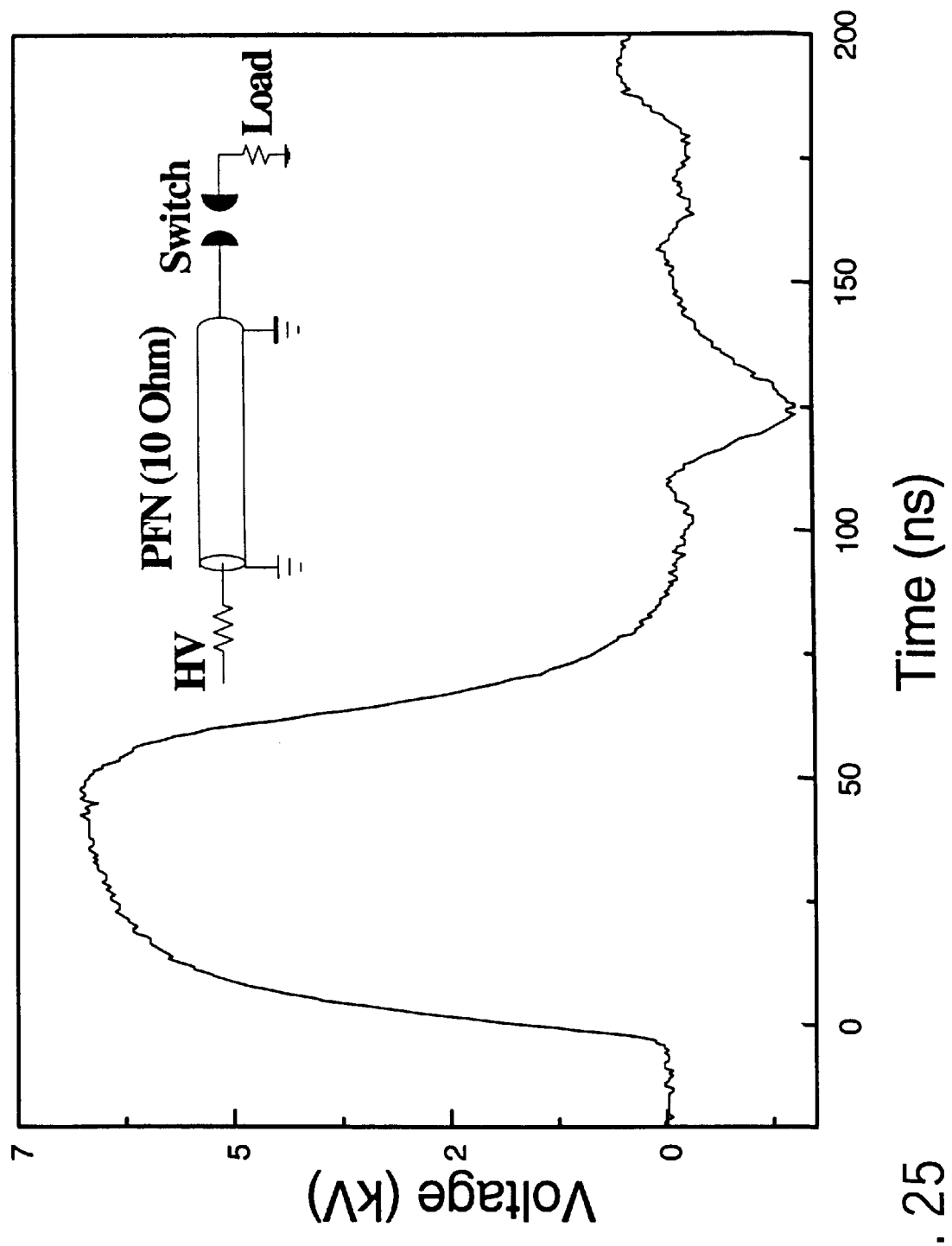
FIG. 25 is graph showing a voltage versus time tracing for an ultra-short electrical pulse produced by the ultra-short pulse generator shown in the inset panel; the resulting electrical pulse is nearly rectangular in shape and reaches a maximum voltage in the 5–6 kV range, which when applied in a cell suspension via electrodes 0.1 cm apart, provides electrical intensities in the 5–6 megavolt/meter range.

A typical ultrashort pulse electric field generator ("USPEF generator") includes a distributed pulse forming network, a switch to allow rapid transfer of electrical energy into the load, and the load itself (see, e.g., FIG. 25, inset). If such a pulse-forming network is charged up to 18 kV, and then released, this charge can produce an almost rectangular ultra-short duration pulse (see FIG. 25), which when applied to a 10 Ω load, produced a maximum voltage of 9 megavolts. The corresponding electric field intensity between two electrodes separated by 1.0 mm is 9 megavolts/m. The maximum electrical power, $V^2/R$, which can be achieved with these conditions is 8.1 MW, while the energy (power x pulse duration) transferred into the load is only 0.49 Joule. For a 100 $\mu$L volume of cell suspension, this energy transfer results in a calculated maximum temperature increase of only about 1° K. for a single pulse.

The following examples are presented to illustrate the present invention and to assist one of ordinary skill in making and using the same. The examples are not intended in any way to otherwise limit the scope of the invention.

EXAMPLE 1

IEM of Neutrophil Suspensions

Experiments were conducted to determine the effects of ultrawide band, low energy, short duration electric pulses (Intracellular Electro-Manipulation or "IEM") to induce a delayed, time-dependent and/or energy/power-dependent cell death in human neutrophils. Groups of cells were subjected to single rectangular pulses having the following parameters and compared to untreated control cells: A4—60 nsec, 6 kV; B6—300 nsec, 4 kV; and B8—300 nsec, 6 kV.

Cells were stained with calcein-AM, a green fluorescent probe that stains the cytoplasm of live, intact cells, and then exposed to the various IEM pulses. Immediately after exposure to IEM, the cells were stained with ethidium bromide homodimer (EtBr), a membrane non-permeable red fluorescent probe that stains the nucleus of cells that exhibit plasma membrane damage. The cells were centrifuged onto glass slides (cytospin). The cells were observed under conditions for calcein (left panel) or EtBr (middle panel) fluorescence (see FIGS. 5–7). Images were captured, and the fields marked. The cells were then stained with Wright stain (right panel), the same fields were observed, and images were captured under conditions for light microscopy. Images were observed at 10× magnification.

Freshly isolated human neutrophils exhibit a limited life span and undergo cell death during in vitro culture. At time 0 (T0) after IEM, only a small percentage of cells (2–5%) exhibits EtBr fluorescence, indicating few membrane-ruptured cells (see FIG. 5a). After 1 hour, a small increase in the number of ruptured cells is indicated. The cells appear as small pinkish (cytoplasm) circles with dark purple dots (nuclei) within.

Figure 5:
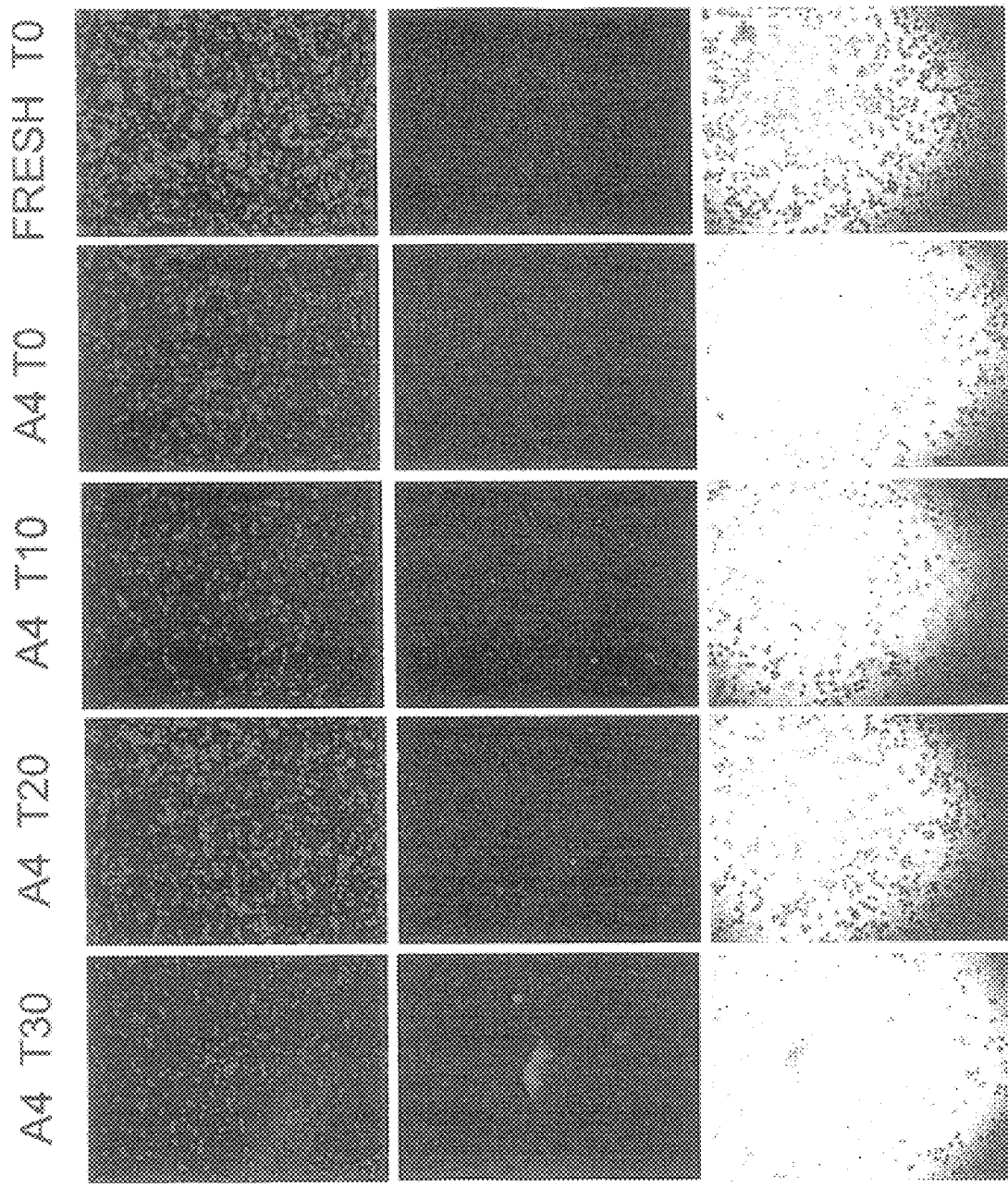
FIG. 5 shows microscopic examinations (10× magnification) of stained human neutrophils at 0, 10, 20 and 30 minutes after being subjected to a 60 nsec, 6 kV electric field pulse ("A4") in comparison to an untreated control (Fresh).

Under A4 pulse parameters at T0 after IEM, no increase in the number of EtBr fluorescent cells is observed, indicating that the cells are still intact (see FIG. 5). A small time-dependent increase in the number of neutrophils exhibiting EtBr fluorescence occurs, indicating small increasing cell death. At T30, there is a small increase in the number of dead cells compared to T30 control cells.

Figure 6:
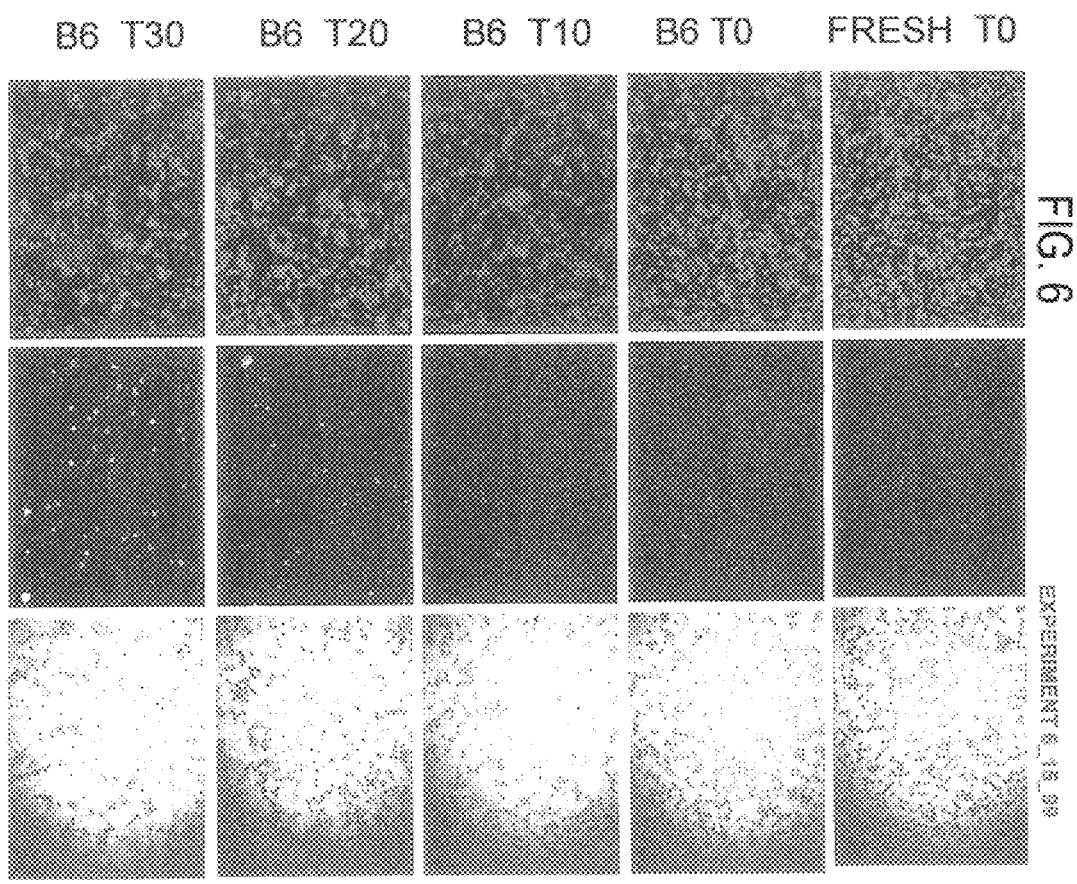
FIG. 6 shows microscopic examinations (10× magnification) of stained human neutrophils at 0, 10, 20 and 30 minutes after being subjected to a 300 nsec, 4 kV electric field pulse ("B6") in comparison to an untreated control (Fresh).

Under B6 pulse parameters at T0 after IEM, no increase in the number of EtBr fluorescence is observed, indicating that the cells are still intact (see FIG. 6). However, a more rapid increase in the number of EtBr fluorescent cells occurs with time. Notice in B6, T20 and T30 (middle panel) there are increases in the percentage of dead cells and in the right panel, increases in the number of lysed, ruptured cells are evident. These appear as pinkish smears (spilled cytoplasm) around dark nuclei. Similar results were observed with the B8 pulse.

EXAMPLE 2

Selective Modification of Subcellular Neutrophil Structures

The ability of IEM to alter subcellular structures without disrupting the plasma membrane was examined. Protease-containing vesicles within the neutrophil were "modified" before the nucleus was "modified," thereby demonstrating selectivity for modifying subcellular structures.

Figure 8:
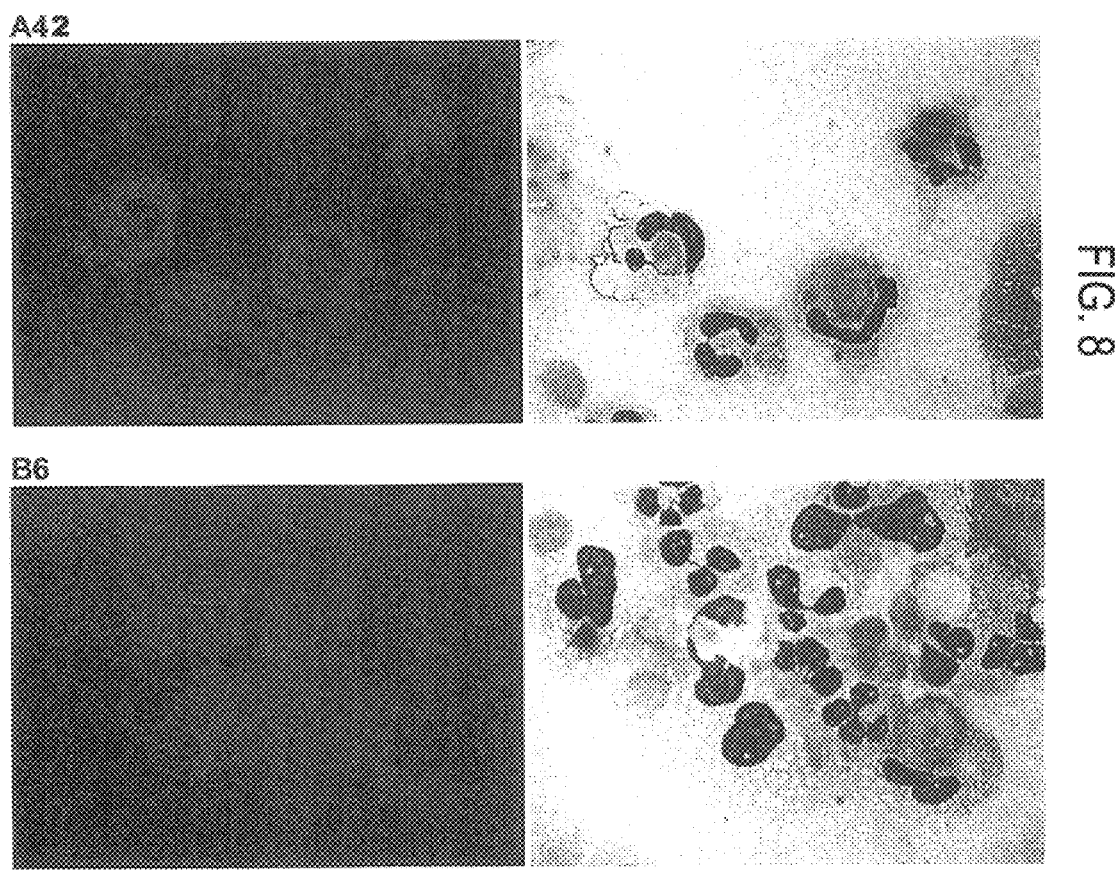
FIG. 8 shows microscopic examinations (280× magnification) of stained human neutrophils immediately after being subjected to a 60 nsec 6 kV electric field pulse, (A4) or 300 nsec 4 kV electric field pulse (B6).
Figure 9:
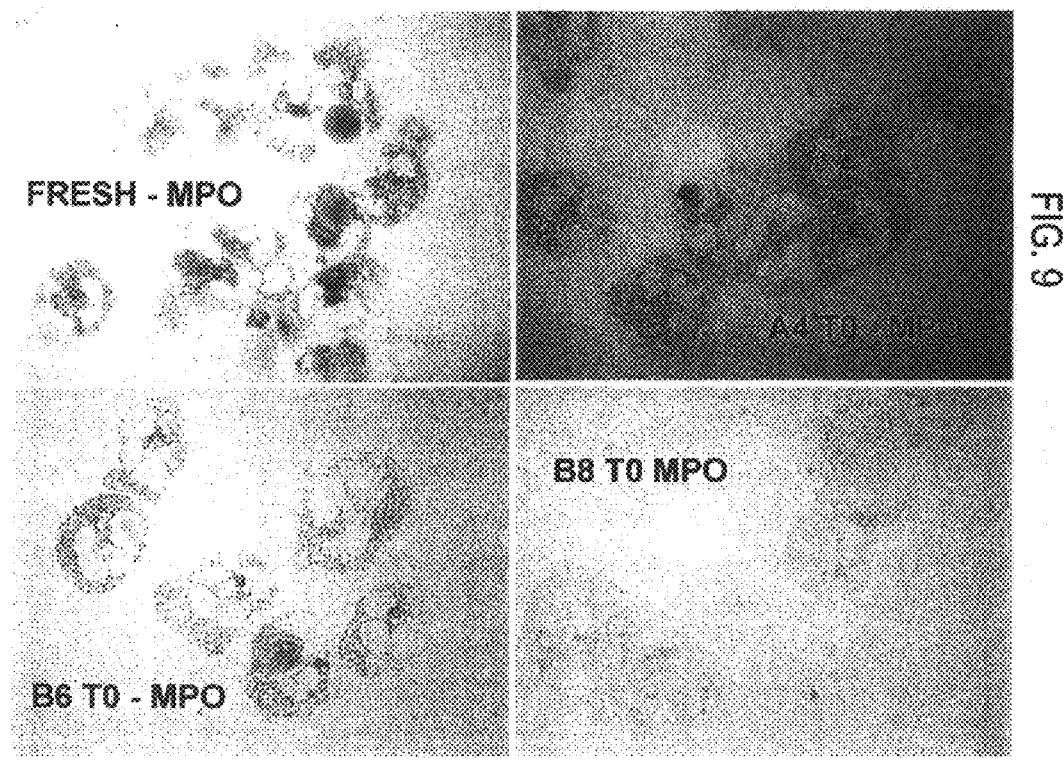
FIG. 9 shows microscopic examination of myeloperoxidase stained human neutrophils (280×magnification) immediately after being subjected to a 60 nsec 6 kV electric field pulse, (A4), 300 nsec 4 kV electric field pulse (B6), or 300 nsec 6 kV electric field pulse (B8) in comparison to untreated control (FRESH).

Method: IEM parameters included sham or control (fresh), A4 (60 nsec, 6 kV), B6 (300 nsec, 4 kV), and B8 (300 nsec, 6 kV). All exposures were at immediately after IEM exposure (T0) and images were at 160×magnification (FIG. 7) or 280×magnification (FIGS. 8 and 9).

Results: FIG. 7. Under A4 pulse parameters at T0 after IEM, no increase in the number of EtBr fluorescence is observed, indicating that the cells are still intact. A4 neutrophils shown are intact and exhibit morphology similar to control cells. The cytoplasm exhibits relatively even fluorescence (left panel) and Wright staining (right panel). Nuclear changes are minimal (dark purple lobed or irregular staining nuclei, surrounded by lighter stained cytoplasm).

In contrast, under B6 pulse parameters at T0 after IEM, the cytoplasm exhibits uneven calcein fluorescence with "pores" or "holes" showing the absence of fluorescence (left panel). Wright staining (right panel) also indicates "pores" or "holes". Nuclear staining appears somewhat uneven, with beginning evidence of "pores" or "holes".

Under B8 pulse parameters at T0 after IEM, cytoplasmic staining is nearly gone and nuclear staining exhibits significant "pores" or "holes" (right panel). The B8 control (left panel, Wright stain) shows neutrophils not exposed to IEM (normal), but prepared at the same time as B8 IEM exposed neutrophils.

B5 (right panel, Wright stain) shows IEM conditions (300 nsec, 3 kV) between A4 and B6. Note how "pores" or "holes" begin to become evident in the cytoplasm. The B5 control (left panel, Wright stain) shows neutrophils not exposed to IEM (normal), but prepared at the same time as B5 IEM exposed neutrophils.

FIG. 8. Neutrophils from A4 and B6 pulse parameters are shown at higher magnification (280×) to more clearly show the cytoplasmic characteristics. The "pores" or "holes" are present in B6, but not A4.

FIG. 9. Neutrophils are shown after myeloperoxidase staining, which stains neutrophil vesicles that contain proteases used for killing bacteria. Myeloperoxidase staining at T0 in fresh and A4 IEM parameter appear relatively granular, indicating the presence of numerous small protease-containing vesicles. Under B6 IEM parameters, the staining is more diffuse, indicating the presence of vesicle rupture. Under B8 IEM parameters, the staining is nearing gone, indicating that nearly all of the vesicles have bee ruptured with the higher energy/power conditions.

EXAMPLE 3

IEM Induces Nuclear Shrinkage in Cells

The ability of IEM to induce nuclear shrinkage in neutrophils and HL-60 cells was examined. Nuclear shrinkage is a typical characteristic of cell death by apoptosis (programmed cell death).

Method: IEM parameters include sham or control (fresh), A4 (60 nsec, 6 kV), B6 (300 nsec, 4 kV), and B8 (300 nsec, 6 kV). Cells were stained with Wright stain immediately after being subjected to the IEM pulse, nuclei were set to gray scale and pixel area was determined. Nucleus sizes from 30 to 42 cells were determined and each one plotted according to pixel area.

Figure 10:
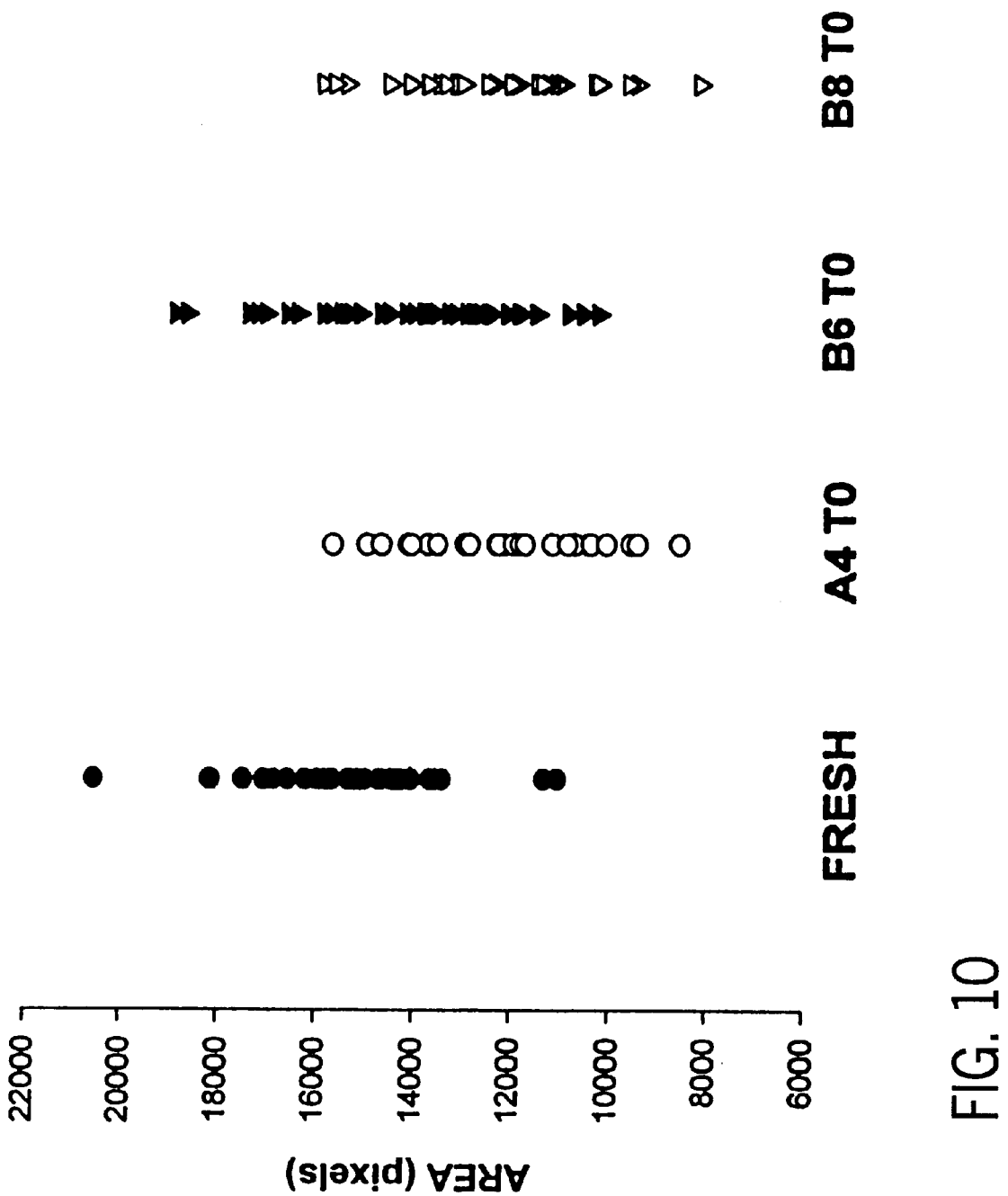
FIG. 10 is a graph of the nuclear area (in pixels) of cells after being subjected to a 60 nsec 6 kV electric field pulse, (A4), 300 nsec 4 kV electric field pulse (B6), or 300 nsec 6 kV electric field pulse (B8) in comparison to untreated control (FRESH).

Result: Nuclei from neutrophils exposed to all three IEM parameters are significantly smaller than control cells (see FIG. 10). The mean nuclear area in pixels for each condition (IEM conditions) were determined. In contrast to the control which had a mean pixel area of 15,152±338 (30 determinations), the cells subjected to an IEM pulse had the following mean pixel areas:

A4-11,871±324 (30 determinations);
B6-13,814±332 (42 determinations); and
B8-12,147±299 (35 determinations). Promyelocytic leukemia HL-60 cells also exhibit nuclear shrinkage (data not shown).

EXAMPLE 4

IEM Selectivity Based on Cell Type

The IEM parameters required to induce cell death in different cell types were examined. Eosinophils were observed to be more sensitive to IEM than neutrophils.

Method: IEM parameters included sham or control (fresh), A4 (60 nsec, 6 kV), B6 (300 nsec, 4 kV), and B8 (300 nsec, 6 kV) as well as additional IEM parameters as indicated. Human neutrophil preparations include some contaminating eosinophils, which are more abundant during hay fever/allergy seasons (at the time of these studies). The number of eosinophils was determined as a percentage of the number of neutrophils by morphology and cell counting under light microscopy.

Result: As the energy/power of IEM is increased, the number of eosinophils present immediately after IEM is significant decreased from the cell population without significant losses of neutrophils (see Table I).

TABLE I

| Slide # | Nsec | kV | neutrophils | eosinophils | % eosinophil |
|---|---|---|---|---|---|
| Fresh | 0 | 0 | 183 | 17 | 9.0 |
| A1 | 60 | 3 | 194 | 6 | 3.0 |
| A2 | 60 | 4 | 190 | 10 | 5.0 |
| A3 | 60 | 5 | 190 | 10 | 5.0 |
| A4 | 60 | 6 | 192 | 8 | 4.0 |
| B5 | 300 | 3 | 188 | 12 | 6.0 |
| B6 | 300 | 4 | 200 | 0 | 0.0 |
| B7 | 300 | 5 | 200 | 0 | 0.0 |
| B8 | 300 | 6 | 199 | 1 | 0.5 |
| B9 | 300 | ˜8 | 200 | 0 | 0.0 |

EXAMPLE 5

Effect of IEM on Chemotaxis

IEM alters neutrophil function without disrupting the plasma membrane. The effects on chemotaxis are different than the effects on unstimulated movement, suggesting a selective effect on neutrophil function.

Method: IEM parameters included sham or control (S), A4 (60 nsec, 6 kV), B6 (300 nsec, 4 kV), and B8 (300 nsec, 6 kV). Cell were exposed to various IEM parameters, placed into wells cut in agarose fill plates, and then induced to crawl in response to control buffer (unstimulated movement) or to a chemical stimulant from bacterial fMLP (chemotaxis). After two hours of movement under agarose, the cells were stained and the absolute density at distances from the origin and mean distance migrated by the neutrophil population were determined by image analysis.

Figure 11:
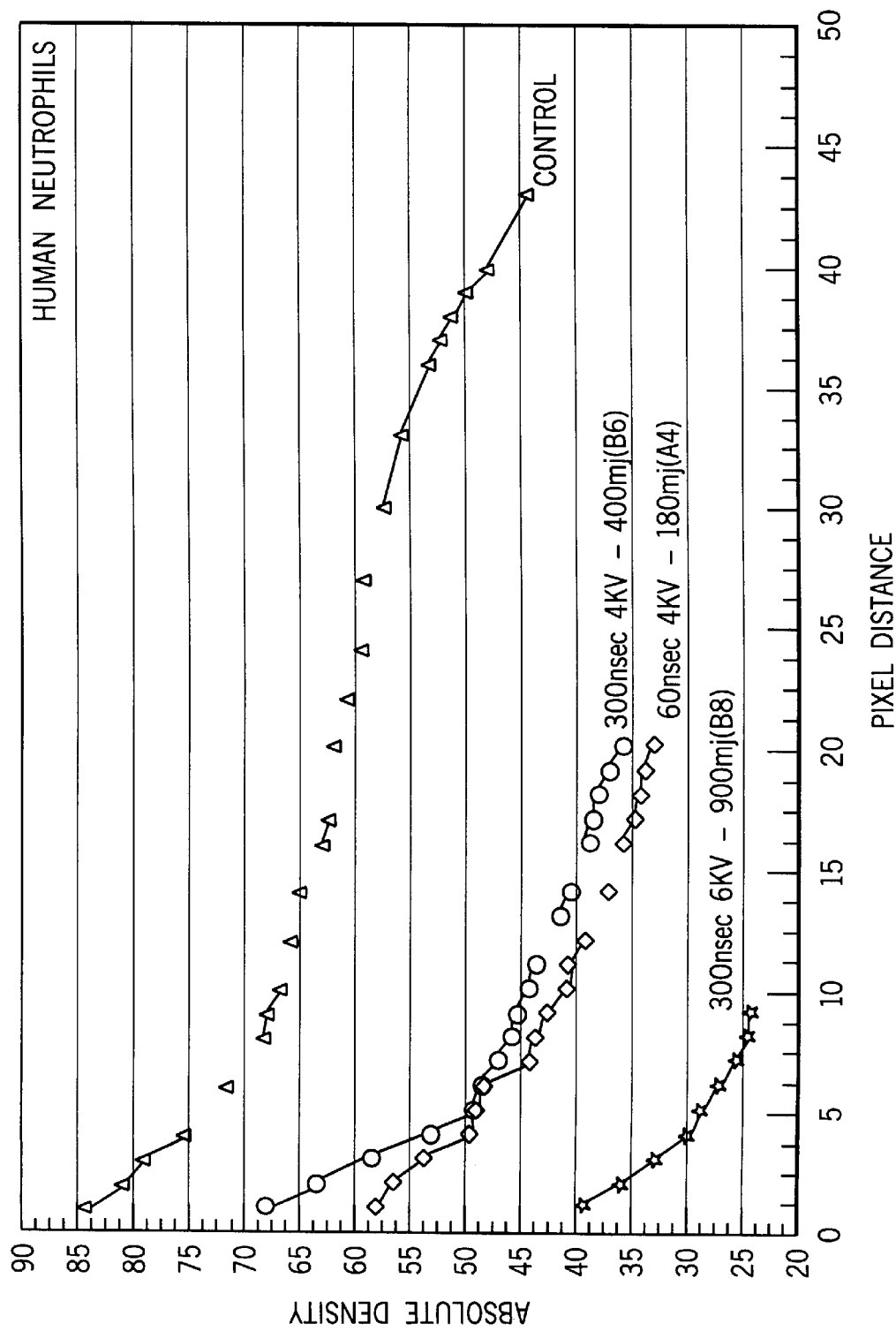
FIG. 11 is a graph of absolute density at distances from its origin for human neutrophils after 2 hours of migration in agarose filled plates in response to bacterial fMLP stimulation; the neutrophils were subjected to a 60 nsec 6 kV electric field pulse, (A4), 300 nsec 4 kV electric field pulse (B6), or 300 nsec 6 kV electric field pulse (B8) in comparison to untreated control (FRESH).
Figure 13:
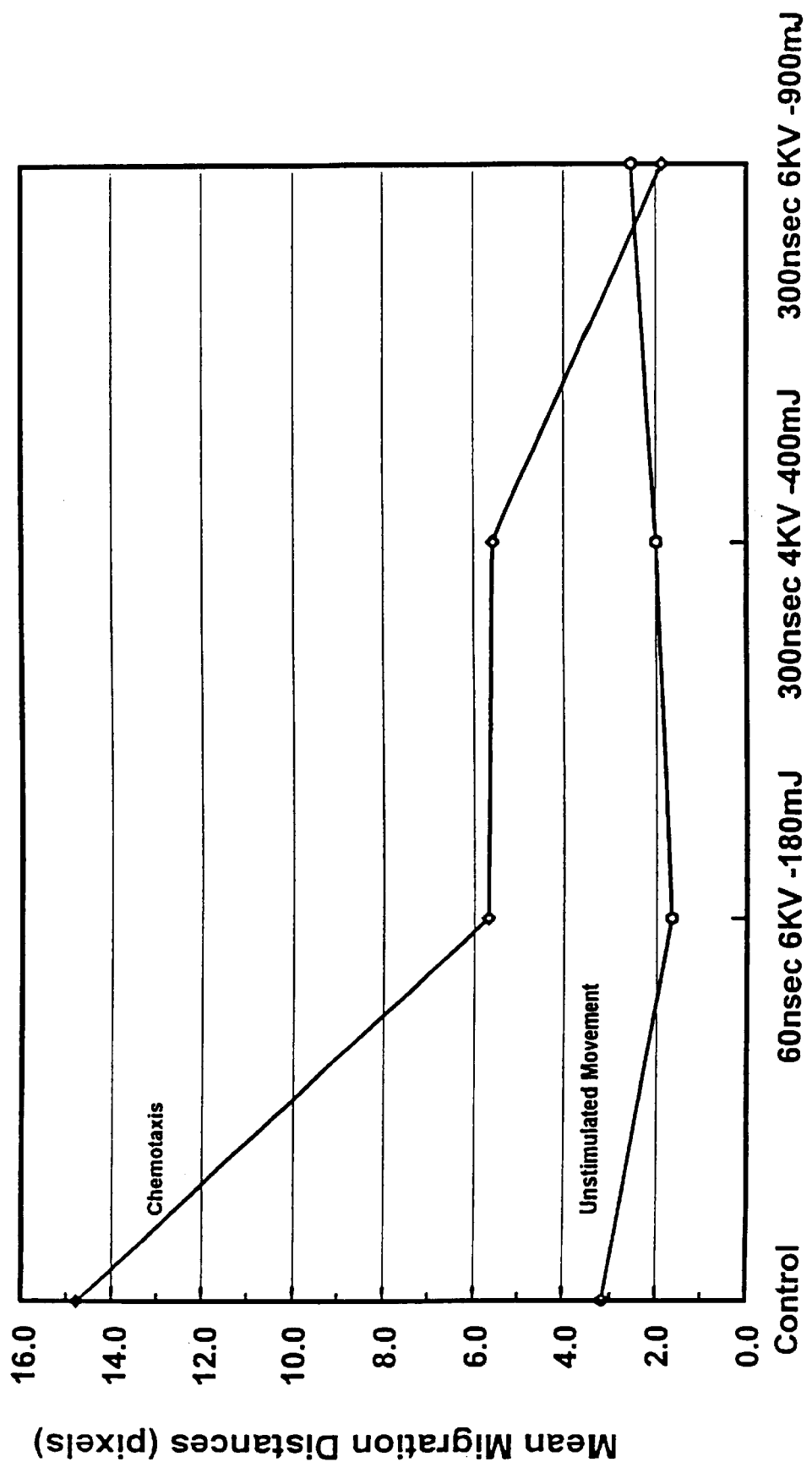
FIG. 13 is a graph of the mean distance migrated by human neutrophils under unstimulated (control buffer) and stimulated (bacterial FMLP) conditions after being subjected to a 60 nsec 6 kV electric field pulse, (A4), 300 nsec 4 kV electric field pulse (B6), or 300 nsec 6 kV electric field pulse (B8) in comparison to untreated control (FRESH).

Result: For chemotaxis, there is a direct relationship between energy/power and inhibition of chemotaxis function; higher energy/power results in increases in chemotaxis inhibition as determined by the absolute density at distances from the origin in each (FIG. 11) and mean distance migrated (FIG. 13). There were 61.6%, 62.4%, and 87.8% inhibition with parameters A4, B6, and B8, respectively, as a percentage of the migration of the bacterial FMLP stimulated control, as determined by the mean distance migrated by the neutrophil population (see Table II).

TABLE II

| Conditions | Chemotaxis | % Inhibition of Chemotaxis | Unstim. Movement |
|---|---|---|---|
| Controls | 14.77 | — | 3.18 |
| 60 nsec, 180 mJ/ml | 5.67 | 61.6 | 1.65 |
| 300 nsec, 400 mJ/ml | 5.56 | 62.9 | 1.98 |
| 300 nsec, 900 mJ/ml | 1.86 | 87.8 | 2.54 |

Figure 12:
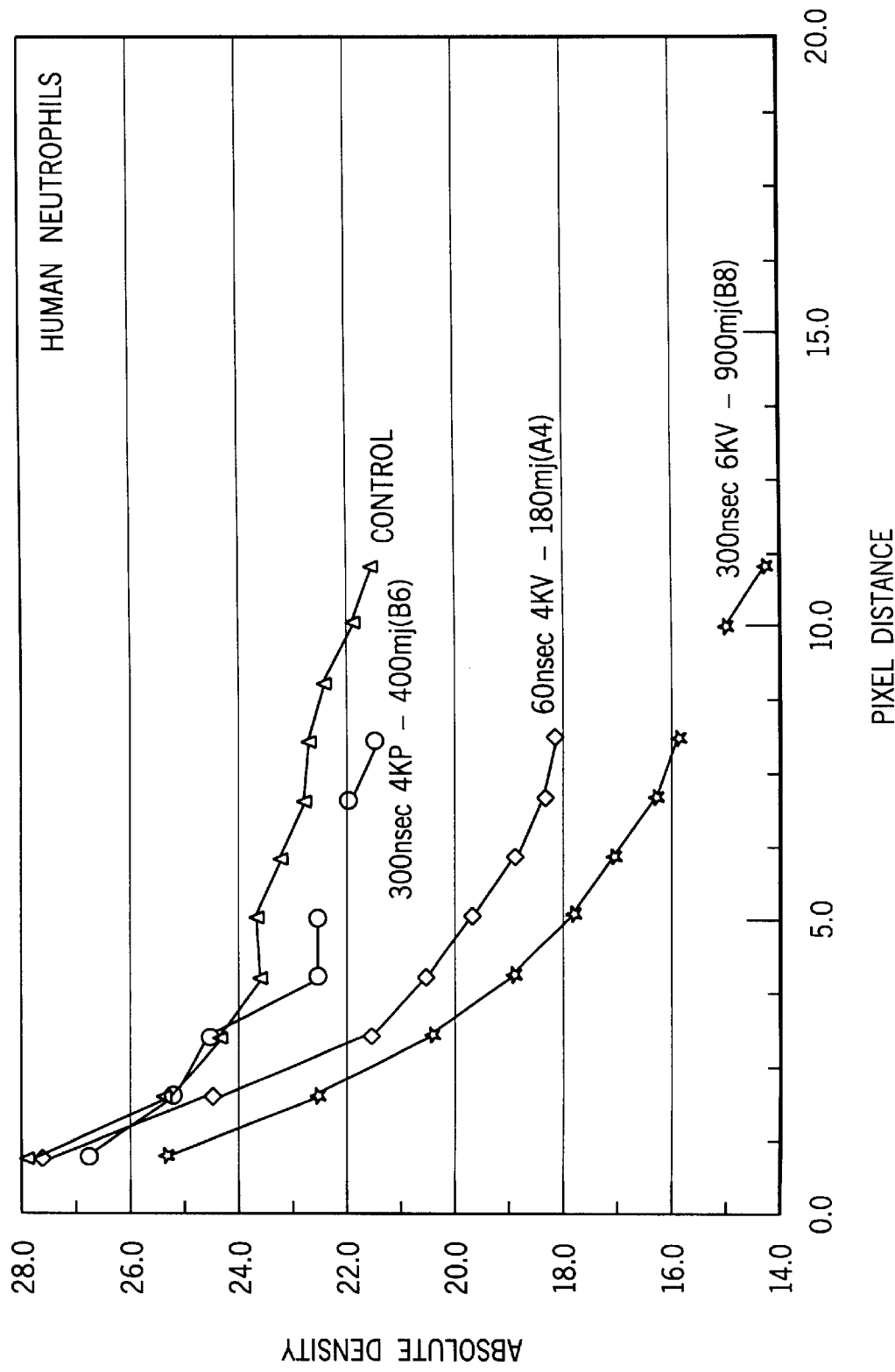
FIG. 12 is a graph of absolute density at distances from its origin for human neutrophils after 2 hours of unstimulated migration (control buffer) in agarose filled plates; the neutrophils were subjected to a 60 nsec 6 kV electric field pulse, (A4), 300 nsec 4 kV electric field pulse (B6), or 300 nsec 6 kV electric field pulse (B8) in comparison to untreated control (FRESH).

In contrast, for unstimulated movement there appears to be little effect between energy/power and inhibition of movement (see FIGS. 12 and 13). The relationship between energy/power of the pulse and inhibition of unstimulated movement is unclear. There were 48.1%, 37.7%, and 20.1% inhibition with parameters A4, B6, and B8, respectively (see Table II), as a percentage of the migration of the unstimulated control.

EXAMPLE 6

The effect of IEM on the proliferation of HL-60 cells in logarithmic growth phase was examined. Proliferation was inhibited by IEM as a function of pulse duration. These results indicate a potential for IEM to selectively kill rapidly growing cells, e.g., tumor cells, Method: HL-60 cells were maintained at a density of 100–300,000 cells/ml, conditions for maximal cell doubling time (10–14 h, log phase growth). Cells were exposed to various IEM parameters by maintaining a constant energy exposure (200–250 mJ/ml) at different pulse durations as indicated. The cells were then diluted to 50,000 cells/ml and the viable cell number (cells that excluded trypan blue; i.e. live cells) was determined after 0, 24, and 48 hours using a hemocytometer under light microscopy.

Figure 14:
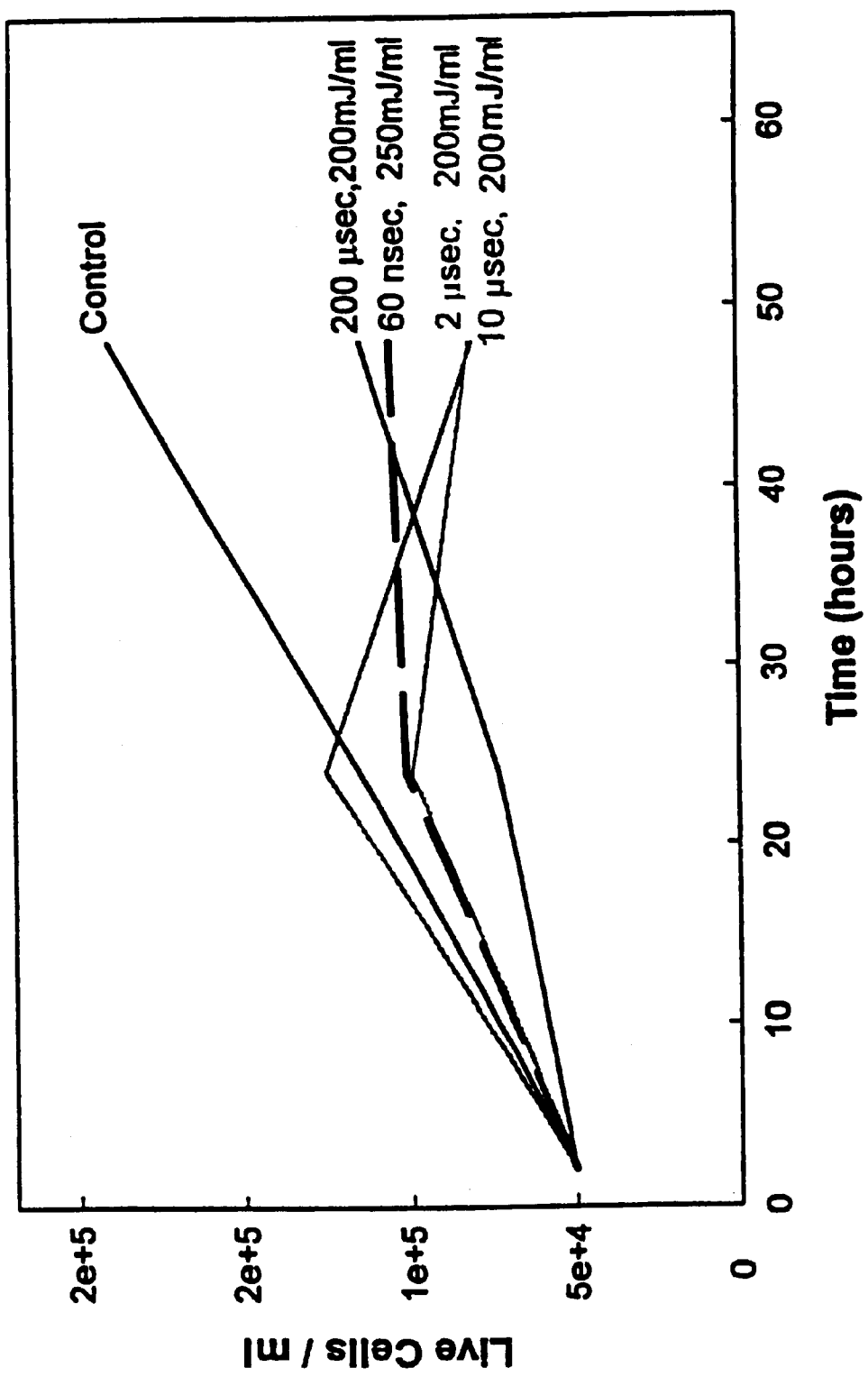
FIG. 14 is a graph showing the effect of exposure of HL-60 promyelocytic leukemia cells in logarithmic growth phase to electric field pulses of varying duration (60 nsec, 2 $\mu$sec, 10 $\mu$sec, or 200 $\mu$sec).

Results: The number of viable cells was not different from control immediately after treatment with IEM (see FIG. 14). Twenty-four hours after IEM, treated cells grew at rates similar to control, except under the condition of the longest pulse time (200 $\mu$sec). After 48 hours, the proliferation rate of cells exposed to a pulse of 0.06–10 $\mu$sec began to decrease, indicating more death events than proliferation events. Cells exposed to a pulse of 200 $\mu$sec increased their proliferation rate to near the control rate.

EXAMPLE 7

Effect of IEM on Cells in Stationary Growth Phase

The effect of IEM on the proliferation of HL-60 cells in the stationary growth phase was examined. Growth was enhanced by IEM as a function of pulse duration. These results indicate a potential for specific IEM conditions to promote the growth of slowly dividing cells.

Method: HL-60 cells were maintained at a density of 1–3,000,000 cells/ml for 3–5 days, conditions for minimal cell doubling time (near stationary phase growth). Cells were exposed to various IEM parameters by maintaining a constant energy exposure (1.7–1.9 J/ml) at different pulse durations as indicated. The cells were then diluted to 50,000 cells/ml and the viable cell number (cells that excluded trypan blue; i.e. live cells) was determined after 0, 24, and 48 hours using a hemocytometer under light microscopy.

Figure 15:
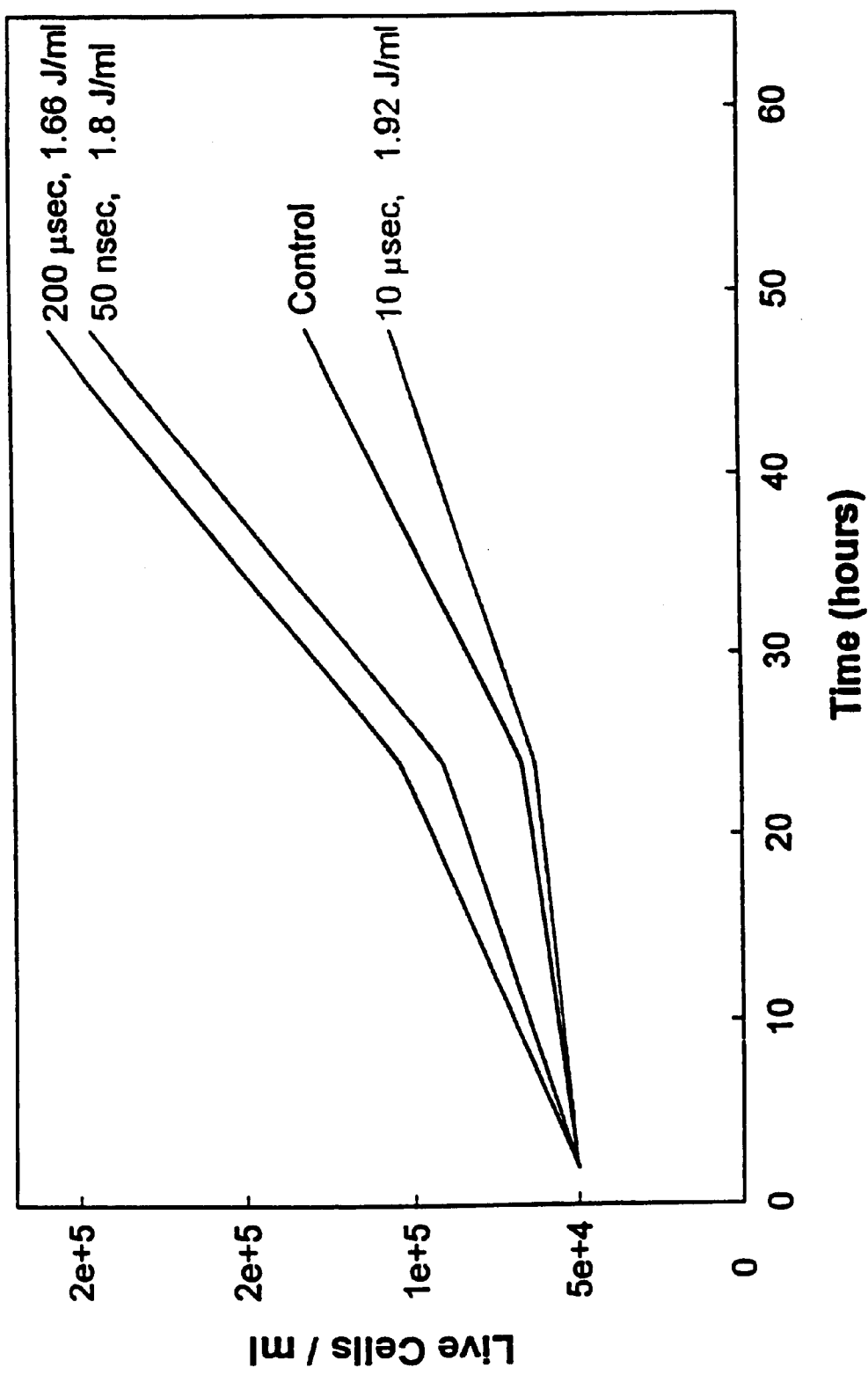
FIG. 15 is a graph showing the effect of exposure of HL-60 promyelocytic leukemia cells in stationary growth phase to electric field pulses of varying duration (60 nsec, 2 $\mu$sec, 10 $\mu$sec, or 200 $\mu$sec).

Results: The number of viable cells was not significant different from control immediately after treatment with IEM (see FIG. 15). After 24 and 48 hours, the proliferation rates were greater than control for cells exposed to a pulse of 0.05 or 200 $\mu$sec. The proliferation rate was less than control for cells exposed to a pulse of 10 $\mu$sec. A pulse duration minimum is observed to inhibit the proliferation of slowly growing cells.

EXAMPLE 8

IEM Induced Apoptosis in Cells

The experiments described in Example 3 above (see FIG. 10) demonstrated that IEM pulses can result in the shrinkage of the nucleus, a hallmark of apoptosis. New data using more specific and definitive markers for apoptosis as well as necrosis, support the hypothesis that IEM pulses induces apoptosis in neutrophils and HL-60 cells.

Method: IEM parameters include sham or control (fresh), A4 (60 nsec, 6 kV, 180 mJ), B6 (300 nsec, 4 kV, 400 mJ), and B8 (300 nsec, 6 kV, 900 mJ). Neutrophils or HL-60 cells were incubated with Annexin-V-FITC and Ethidium bromide homodimer ("EtBr"). Annexin-V-FITC binding was used as a quantitative apoptosis marker. Annexin-V exhibits calcium-dependent binding to phosphatidylserine. While phosphatidylserine is typically restricted to the inner leaflet of the cell membrane in normal cells and is therefore inaccessible to Annexin-V in solution, apoptotic cells express phosphatidylserine in their outer membrane leaflet, resulting in ready binding of Annexin-V to their surfaces. EtBr binds to DNA, but is impermeable to the cell membrane. EtBr fluorescence occurs only in cells that have ruptured membranes. Therefore, apoptotic cells exhibit only Annexin fluorescence while necrotic cells exhibit fluorescence for EtBr plus or minus Annexin fluorescence. Cells are exposed to IEM and at the indicated times after IEM, cells are evaluated by fluorescence microscopy, counted, and expressed as percent cells showing apoptosis and necrosis.

Figure 16:
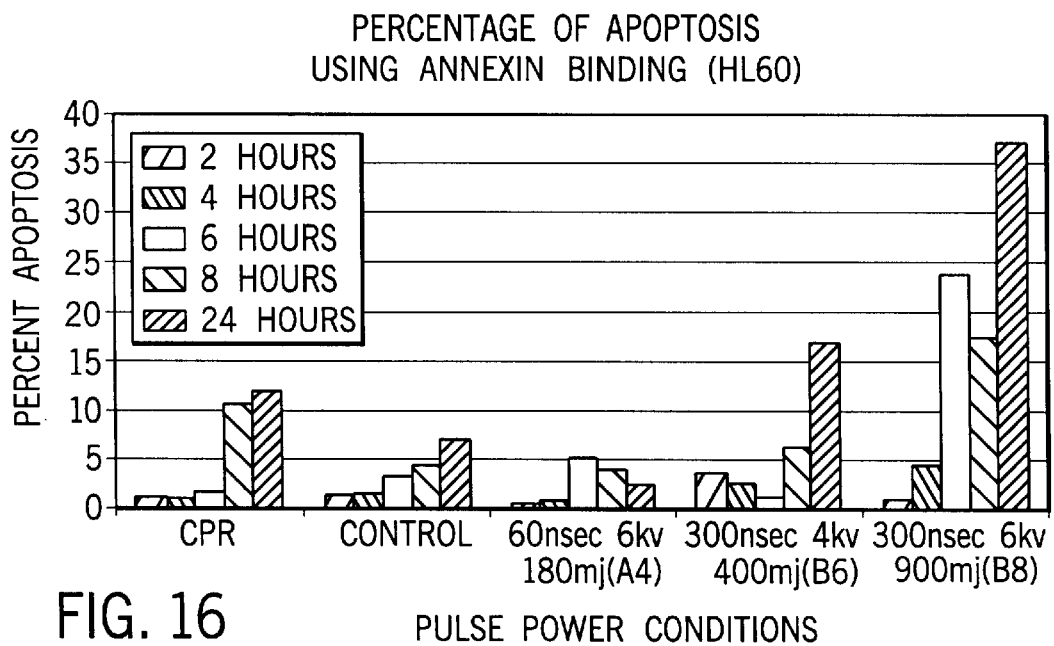
FIG. 16 is a graph showing the percentage apoptosis of HL-60 cells as a function of time after being subjected to IEM pulses at 60 nsec, 6 kV (A4), 300 $\mu$sec, 4 kV (B6) or 300 $\mu$sec, 6 kV (B8).
Figure 17:
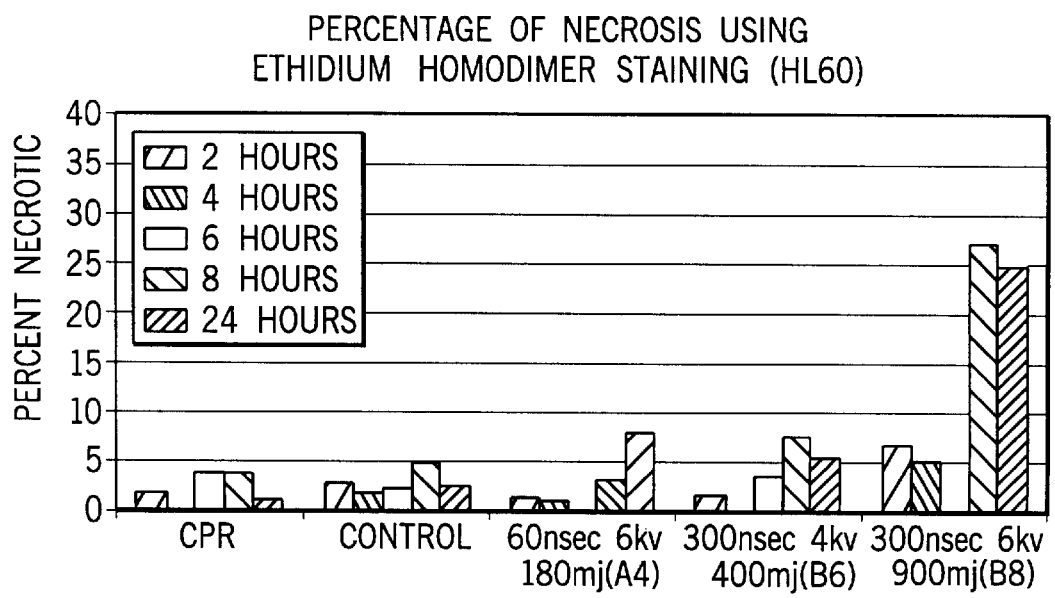
FIG. 17 is a graph showing the percentage necrosis of HL-60 cells as a function of time after being subjected to IEM pulses at 60 nsec, 6 kV (A4), 300 μsec, 4 kV (B6) or 300 μsec, 6 kV (B8).
Figure 18:
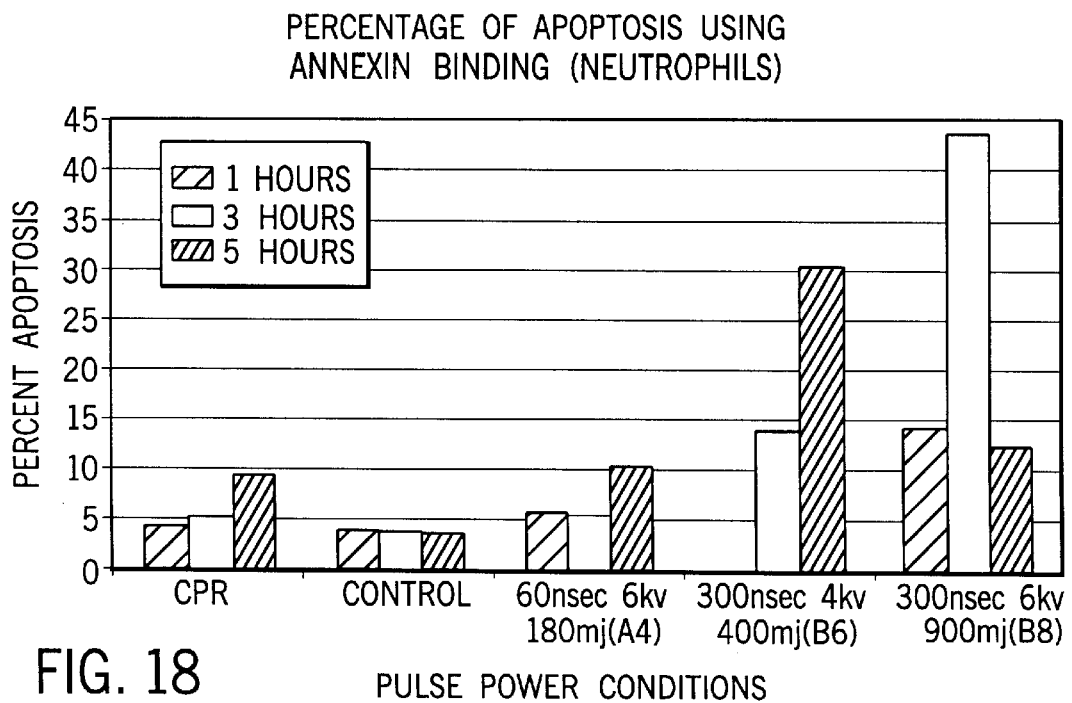
FIG. 18 is a graph showing the percentage apoptosis of human neutrophils as a function of time after being subjected to IEM pulses at 60 nsec, 6 kV (A4), 300 μsec, 4 kV (B6) or 300 μsec, 6 kV (B8).
Figure 19:
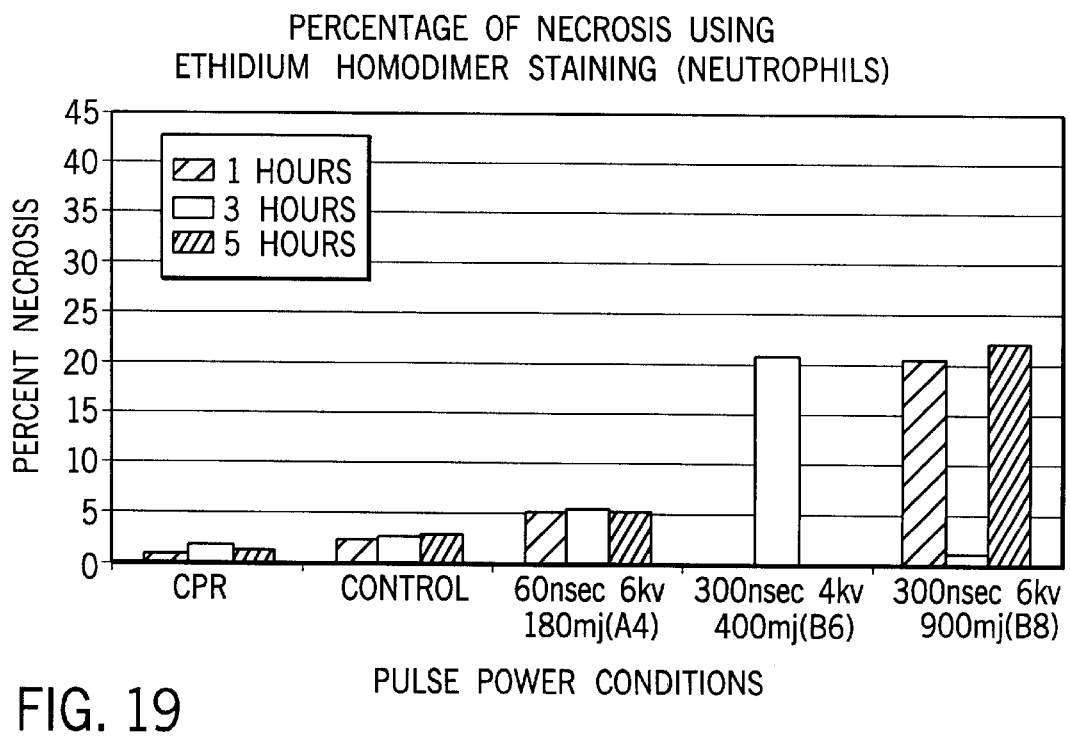
FIG. 19 is a graph showing the percentage necrosis of human neutrophils as a function of time after being subjected to IEM pulses at 60 nsec, 6 kV (A4), 300 μsec, 4 kV (B6) or 300 μsec, 6 kV (B8).

Results: Control cells (human neutrophils) do not exhibit significant markers for apoptosis or necrosis during the time course of the experiment (see FIGS. 16 and 17). This indicates that these pulses do not kill the cell by membrane rupture. HL-60 cells exposed to IEM conditions A4, B6, and B8 show a time-dependent and an energy- or power-dependent increase in apoptosis. In A4, B6, and B8, cells begin to show the apoptosis marker after 5, 3, and 1 hours, respectively (see FIG. 16). As the apoptotic cells proceed to cell death, necrosis occurs, secondary to apoptosis (see FIG. 17). This is indicated by the appearance of necrosis only after apoptosis. Secondary necrosis is an in vitro-specific effect. In vivo, the apoptotic cells are remove by phagocytosis before necrosis and inflammation occur. FIGS. 18 and 19 show similar results for human neutrophils.

EXAMPLE 9

Effect of IEM Treatment on Calcein-AM Stained Cells

Free calcein is a highly fluorescent modified fluorescein with 6 negative and 2 positive charges that is membrane impermeant. In its methyl ester form, calcein-AM, it is non-fluorescent and membrane permeable. When used as a fluorescent stain for cells, calcein-AM passes through the surface membrane and is cleaved to free calcein+the methyl ester residue by intracellular esterase activities. This modification traps the free calcein in the cytoplasm of the cell, and retention of the free calcein is a common criterion for intactness of the surface membrane. In addition to remaining trapped within the cell, the intracellular free calcein also remains excluded from other intracellular membrane-bound compartments because of its membrane impermeant nature (an effect illustrated in calcein-AM labeled eosinophils which show bright cytoplasmic free calcein fluorescence and "negative staining" of their large intracellular granules).

Aliquots of an eosinophil-enriched leukocyte preparation (65% eosinophils) were exposed to 1 $\mu$M free calcein in HBSSw/o plus increasing amounts (0%–0.05%) Triton X-100 (5 minutes, 25° C.) and examined microscopically. Eosinophils exposed to free calcein without Triton showed no calcein staining consistent with the membrane impermeant characteristics of free calcein. Red eosinophil autofluorescence was readily visible and was also visible in all conditions up to and including the free calcein +0.01% Triton exposure. However, in the free calcein +0.01% Triton condition, occasional eosinophils showed an isolated bright green granule within the eosinophil autofluorescence pattern. In the free calcein +0.05% Triton condition, fluorescent illumination revealed many discrete areas of pale green fluorescence with overlying, bright green punctate areas of fluorescence. After Wright-Giemsa staining, these were recognized to be the residual nuclei of fully detergent-solubilized cells (pale green fluorescence) with associated eosinophilic granules corresponding exactly to the punctate areas of bright fluorescence (see FIG. 26). These results illustrated that detergent-treated eosinophil granules stained brightly with free calcein, presumably due to interaction between cationic eosinophil granule components and the anionic free calcein, and paralleled results of others using fluorescein-labeled antibodies.

Calcein-AM stained eosinophils trap free calcein in their cytoplasm after staining (left), and the intracellular free calcein is excluded from the eosinophil's large granules as shown on the left. Without Triton treatment, free calcein is incapable of staining eosinophil cytoplasm (center): only eosinophil autofluorescence visible. With incubation in 0.001% Triton, free calcein continues to be excluded from eosinophils, but stains the fine granules of a PMN showing obvious detergent effects (right) (see FIG. 26). With 0.005% Triton treatment (left), the morphology of some eosinophils suggests partial detergent solubilization which is accompanied by bright free calcein staining of eosinophil granules, and detergent solubilized PMN show very fine, fluorescent "calcein sand" staining patterns. With 0.01% Triton +1 $\mu$M free calcein treatment (center), all eosinophils show nuclear changes suggestive of detergent effect, and many contain 1–2 bright granules on a background of red autofluorescence. With 0.05% Triton X-100+1 $\mu$M free calcein treatment, only eosinophil nuclear remnants are seen (right, top), some with associated eosinophilic granules which are brightly fluorescent with free calcein (right, below).

A typical pulse generator for producing USPEF effects is illustrated in FIG. 25, and consists of a pulse forming network (typically a coaxial cable or a strip line), a switch and the load. In the case of a matched load (resistance of the load=the impedance of the pulse forming network), the voltage pulse across the load has an amplitude of half the voltage applied to the pulse-forming network (for the experiments described, the pulse-forming network comprised 5 high voltage 50 $\Omega$ cables in parallel, which achieved the required 10 $\Omega$ impedance for matched operation). The pulse duration is twice the length of the cable or strip line, divided by the speed of the electromagnetic wave in the dielectric of the pulse-forming network. The switch is a simple spark gap in atmospheric air. The breakdown voltage is set by varying the gap distance. The load consists of the 100 $\mu$L of cell suspension to be exposed to the USPEF, and when Hanks Balanced Salt Solution without $Ca^{++}$ and $Mg^{++}$ (HBSSw/o) is used to suspend the cells, has an electrical resistivity of 100 $\Omega$cm. The load is placed in an electroporation cuvette (BioRad, Inc., Hercules, Calif.) constructed with parallel plate aluminum electrodes 1 $cm^2$ in area and separated by 0.1 cm, resulting in a load resistance R=10 $\Omega$.

Polymorphonuclear leukocytes (PMN) were purified from heparinized blood was obtained from adult volunteer donors, using hypaque-ficoll sedimentation, dextran sedimentation and hypotonic lysis. These cell preparations were typically 92–95% PMN, 5–8% eosinophils and 1–3% mononuclear cells. Following purification, PMN preparations were labeled with 1 $\mu$M calcein-AM (Molecular Probes, Inc. Eugene, Oreg.) according to the manufacturer's directions, washed and adjusted to $20\times10^6$/ml in Hanks Balanced Salt Solution without $Ca^{++}$ or $Mg^{++}$ (HBSSw/o).

Immediately following USPEF application, cells were removed from the cuvette, diluted 1:4 in HBSS with $Ca^{++}$ and $Mg^{++}$ (HBSSw) and applied to glass slides (1000 rpm, 5 minutes) using a Cytospin 3 (Shandon Southern, Sewickley, Pa.). Multiple slide preparations for each pulse condition were prepared (1000 rpm, 5 minutes) and kept in a sealed box until examined microscopically. Microscopic examinations used either an Olympus BH-1 photomicroscope with a Kodak DC-120 digital camera, or an Olympus IX70 inverted microscope with an OlymPix CCD video camera at 100×magnification.

Initial experiments used PMN labeled with calcein-AM to achieve fluorescent labeling of the cytoplasm and showed that single USPEF applications of either 3.6 or 5.3 megavolts/m could effect intracellular free calcein distributions and the Wright-Giemsa stained morphology in these cells assessed microscopically. Multiple USPEF applications induced subjective changes in both intracellular free calcein distributions and Wright-Giemsa stained PMN morphology, but the most striking effect was seen in eosinophils contaminating the PMN preparations. "Sparkler" cells (cells with cytoplasmic calcein staining plus centrally-located, large, bright fluorescent granules) were seen with both electric field intensities when $\geq 3$ USPEF applications were used (see Table 1). When examined by Wright-Giemsa stain, the "sparkler" cells were always eosinophils, and often appeared "shrunken" relative to the appearance of eosinophils in the control condition.

Figure 27:
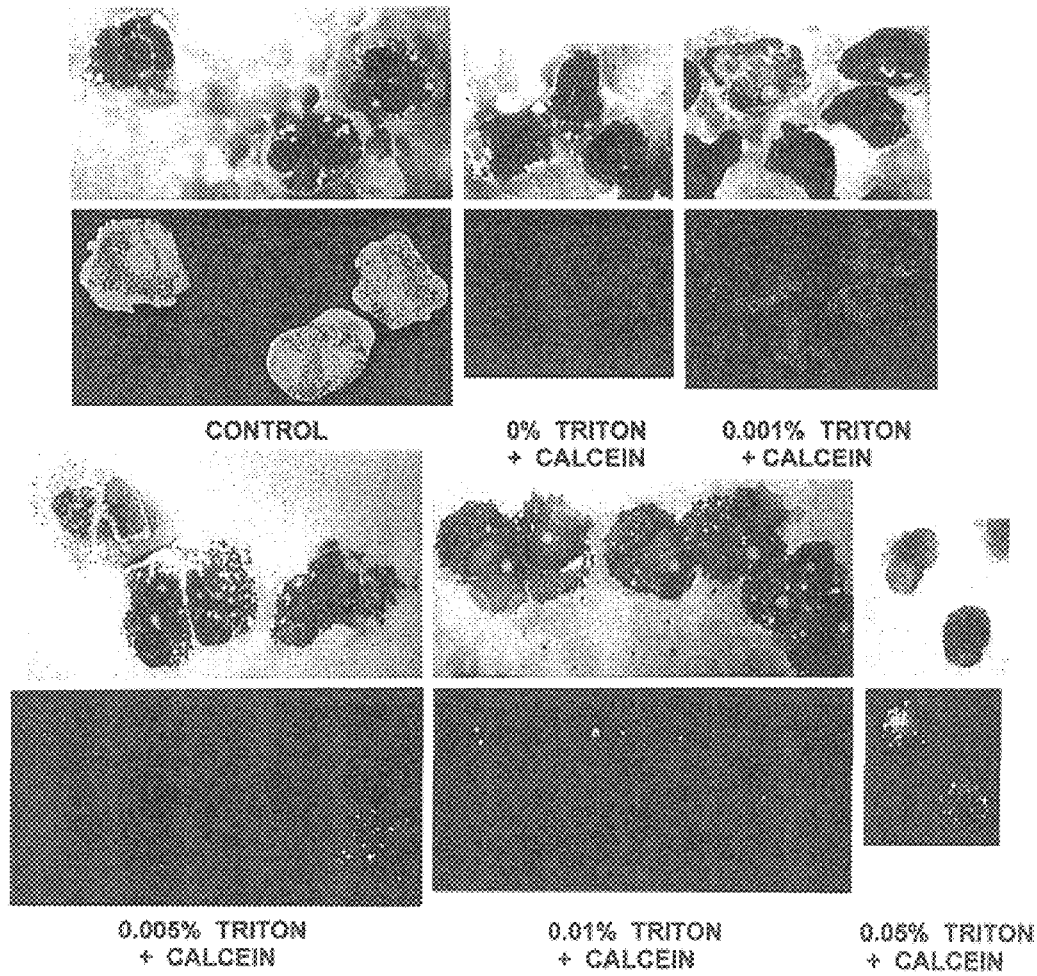
FIG. 27 shows microscopic examination of an eosinophil preparation exposed to USPEF treatments (60 nsec 5.3 megavolt/m ×3 (middle) and ×5 (below) versus control eosinophils labeled with calcein-AM (top).

Recognizing that intense free calcein staining of eosinophils granules could only occur if granule membrane integrity was lost, two eosinophil-enriched leukocyte preparation (65% and 87% eosinophils) were USPEF exposed (60 nsec, 5.3 megvolts/m×3 or ×5) and examined the cells microscopically (see FIG. 27). Control cell preparations stained with calcein-AM showed eosinophils with bright cytoplasmic free calcein staining and exclusion of free calcein from their intracellular granules.

FIG. 27 shows "sparkler" cells in an eosinophil preparation exposed to USPEF treatments (60 nsec 5.3 MV/m×3 (middle) and ×5 (below). Control eosinophils labeled with calcein-AM (top) show bright cytoplasmic free calcein staining with exclusion of fluorescence from intracellular granules. Application of multiple USPEF treatments to this cell preparation results in appearance of "sparkler" cells with bright cytoplasmic free calcein staining (indicating that the surface membrane is intact) and bright fluorescence of some intracellular granules, indicating that intracellular free calcein has gained access to and labeled the cationic intragranular components. The middle panels also illustrate the "shrunken" eosinophil morphology frequently noted in the 60 nsec 5.3 MV/m×3 and ×5 conditions. A normal sized eosinophil with bright cytoplasmic free calcein staining/ unstained granules is at right, and 3 "shrunken" eosinophils, all "sparkler" cells, are on the left.

After USPEF exposures in both conditions, 39% and 77% (3 USPEF exposures), and 42% and 58% (5 USPEF exposures) of all cells had "sparkler" characteristics (strong cytoplasmic free calcein staining plus subpopulations of central, brightly fluorescent intracellular granules) and were eosinophils on subsequent Wright-Giemsa staining. Considering the degree of eosinophil enrichment in the test preparations, 76–84% (3 USPEF exposures) and 59–71% (5 USPEF exposures) of total eosinophils had acquired "sparkler" characteristics following these treatments.

Eosinophil granules contain a variety of cationic proteins which could potentially bind the highly anionic free calcein if the granule membrane were breached, as shown in the Triton solubilization experiment. Therefore, we conclude that development of "sparkler" morphology in calcein-AM loaded eosinophils following repeated USPEF applications is the result of selective poration/disruption of the eosinophil granule membrane during USPEF applications, which allowed cytoplasmic free calcein to enter the granule and bind to the cationic granule components. We interpret this as strong evidence that selective poration/disruption of intracellular membranes without loss of surface membrane integrity can be achieved with USPEF applications.

EXAMPLE 10

IEM of Mouse Fibrosarcoma Cells

Seven to 8 week old immunocompetent C57B1/6 mice were inoculated subcutaneously with $1.5\times10^6$ B10.2 mouse fibrosarcoma cells in 0.1 ml PBS using a 1 cc syringe fitted with a 27-gauge needle. The injection site was either in the flank region or on the back of the animal. Two to three weeks later the tumors were excised and sliced into two pieces along the equatorial axis. One piece served as a matched control and the other piece was exposed to three pulses each at 300 nsec and 6 kV (900 mJ).

Tumor slices (0.1 cm thickness) were placed in an electroporation cuvette between two electrodes spaced 0.1 cm apart and Hank's balanced salt solution was added to fill the cuvette. The tissues were exposed to pulses as indicated, removed, and prepared for analysis. The tissues were incubated for 5 hours at 37° C. in RPMI media with 10% fetal bovine serum. The tissues were then fixed in 10% buffered formalin for 18 hours. The air was removed from the tissues using a vacuum and the degassed tissues were embedded in paraffin. Four micron slices were prepared and placed on glass slides pretreated with 2% APES in acetone. The paraffin was removed by successive washes in xylene, absolute ethanol, 95% ethanol, 70% ethanol, and PBS. The tissue slices were incubated with proteinase K (40 ug/ml) for 15 minutes at 40° C.

The tissue slides were prepared for examination of DNA fragmentation as a marker for apoptosis using a rhodamine-labeled sheep anti-digoxigenin antibody (Apop-tag™ from Intergen) and fluorescence microscopy according to the manufacturers protocol. The slides were counterstained with DAPI. Normal nuclei were stained blue by DAPI and apoptotic nuclear were stained red with rhodamine. Two to three hundred cells were counted and scored as blue (normal) or red (apoptotic). The apoptotic index is defined as the number of apoptotic nuclei divided by the total number of nuclei. The results are shown in Table IV below.

TABLE IV

Apoptosis of Mouse Fibrosarcoma

| | Total Cells | Apoptotic Nuclei | % Apoptosis (Apoptotic Index) | Average % Apoptosis |
|---|---|---|---|---|
| Control | 257 | 10 | 3.9 | 5.8 ± 0.7 |
| | 227 | 14 | 6.2 | |
| | 248 | 16 | 6.5 | |
| | 229 | 20 | 6.7 | |
| Post | 280 | 91 | 32.5 | 35.0 ± 2.2 |
| IEM | 243 | 96 | 39.5 | |
| | 294 | 89 | 30.3 | |
| | 258 | 97 | 37.6 | |

(Following Electromanipulation)

Table IV illustrates the apoptotic index (percentage of apoptotic cells) in a representative tumor that was exposed to three consecutive 300 nsec pulses at 6 kV in comparison to an unpulsed control. About 6% of the nuclei from the control tumor were apoptotic when sampled from four different sections of the same tumor. In contrast, 35% of the nuclei were apoptotic from the tumor exposed to the sequence of ultra-short, high intensity pulses. This represents a 6-fold increase in apoptotic nuclei after exposure to these pulses. In a total of 6 tumors from different animals, a 3–6-fold increase in apoptotic nuclei were observed in tumors exposed to the electric field pulses, although the absolute number of apoptotic nuclei in untreated tumors varied from 4% to 30%. No differences were observed between control and treated tumor tissues when three consecutive pulses at 60 nsec and 6 kV were compared (data not shown). These results indicate that ultra-short, high intensity pulses can induce apoptosis in tumor tissue.

Throughout this application various publications are referenced. The disclosures of these publications in their entireties are hereby incorporated by reference into this application in order to more fully describe the state of the art to which this invention pertains.

The invention has been described with reference to various specific and illustrative embodiments and techniques. However, it should be understood that many variations and modifications may be made while remaining within the spirit and scope of the invention.

TABLE III

Effects of USPEF Treatments of Human Blood Eosinophils in PMN Preparations.

| | | USPEF Conditions* | | | | | |
|---|---|---|---|---|---|---|---|
| Effect | None | 3.6 MV/m 60 nsec × 1 | 3.6 MV/m 60 nsec × 3 | 3.6 MV/m 60 nsec × 5 | 5.3 MV/m 60 nsec × 1 | 5.3 MV/m 60 nsec × 3 | 5.3 MV/m 60 nsec × 5 |
| Shrunken eosinophils (n) | 0 ± 0% (6) | 0 ± 0% (3) | 1 ± 1% (3) | 1 ± 1% (4) | 8 ± 3% (3) | 59 ± 12% (5) | 55 ± 5% (7) |
| "Sparkler" cells (% of all cells) (n) | 0 ± 0% (3) | 2 ± 2% (3) | 4 ± 1% (3) | 2 ± 1% (3) | 5 ± 2% (3) | 9 ± 5% (3) | 5 ± 1% (3) |
| Eosinophils (% of all cells) (n) | 7 ± 3% (3) | 6 ± 2% (3) | 7 ± 1% (3) | 7 ± 3% (3) | 6 ± 1% (3) | 10 ± 2% (3) | 6 ± 1% (3) |

*Multiple USPEF exposures were triggered manually at approximately 1 second intervals.

What is claimed is:

1. A method for initiating apoptosis in target cells comprising applying at least one ultrashort electric field pulse to the target cells, whereby apoptosis is initiated in said target cells;
   wherein each ultrashort electric field pulse has a pulse duration of at least about 100 picoseconds and no more than about 1 microsecond.

2. A method for destroying target cells comprising applying to said target cells one or more ultrashort electric field pulses of sufficient amplitude and duration to collectively activate annexin binding on an outer cell surface membrane of said target cells without causing an immediate, irreversible disruption of the outer cell surface membrane in said target cells, whereby destruction of said target cells is initiated;

wherein each ultrashort electric field pulse has a pulse duration of about 100 picoseconds to about 1 microsecond.

3. A method for destroying target cells comprising applying to said target cells one or more ultrashort electric field pulses of sufficient amplitude and duration to collectively cause shrinkage of said target cells without causing an immediate, irreversible disruption of an outer cell surface membrane in said target cells, whereby destruction of said target cells is initiated;

wherein each ultrashort electric field pulse has a pulse duration of about 100 picoseconds to about 1 microsecond.

4. The method of claim 3 wherein each ultrashort electric field pulse is a rectangular pulse or a trapezoidal pulse.

5. The method of claim 3 wherein each ultrashort electric field pulse has a Fourier spectrum which includes frequencies with amplitudes greater than $V_{MAX}/2$ between about 1 MHz and about 1 GHz.

6. The method of claim 3 wherein the ultrashort electric field pulse has a rise time of no more than about 50 nsec.

7. The method of claim 3 wherein each ultrashort electric field pulse has a rise time which is no more than about 20% of its pulse duration.

8. The method of claim 3 wherein each ultrashort electric field pulse has a total energy of a total energy of at least about 10 mJ/cc.

9. The method of claim 8 wherein each ultrashort electric field pulse has a total energy of no more than about 10 J/cc.

10. The method of claim 3 wherein each ultrashort electric field pulse has an amplitude of at least about 20 kV/cm.

11. The method of claim 10 wherein each ultrashort electric field pulse has an amplitude of no more than about 1 MV/cm.

12. The method of claim 3 wherein the target cells are suspended in a medium.

13. The method of claim 3 wherein the target cells are included in a tissue.

14. The method of claim 3 wherein each ultrashort electric field pulse has a pulse duration of about 1 nanosecond to about 500 nanoseconds.

15. The method of claim 3 wherein the target cells are eukaryotic cells.

16. The method of claim 15 wherein the eukaryotic cells include cancer cells.

17. The method of claim 16 wherein the cancer cells are leukemia cells or fibrosarcoma cells.

18. The method of claim 15 wherein the eukaryotic cells include fat cells, bone cells, vascular cells, muscle cells, cartilage cells or a combination thereof.

19. The method of claim 3 wherein each ultrashort electric field pulse has a pulse duration of about 10 to about 300 nanoseconds and a pulse amplitude of about 20 kV/cm to about 500 kV/cm.

20. A method for destroying target cells in a tissue comprising applying to said target cells one or more ultrashort electric field pulses of sufficient amplitude and duration to collectively cause nuclear shrinkage of said target cells without causing an immediate, irreversible disruption of an outer cell surface membrane in said target cells, whereby destruction of said target cells is initiated;

wherein each ultrashort electric field pulse has wherein each ultrashort electric field pulse has a pulse duration of about 10 to about 500 nanoseconds and a pulse amplitude of about 20 kV/cm to about 300 kV/cm.

21. The method of claim 2 wherein each ultrashort electric field pulse is a rectangular pulse or a trapezoidal pulse.

22. The method of claim 2 wherein each ultrashort electric field pulse has a Fourier spectrum which includes frequencies with amplitudes greater than $V_{MAX}/2$ between about 1 MHz and about 1 GHz.

23. The method of claim 2 wherein the ultrashort electric field pulse has a rise time of no more than about 50 nsec.

24. The method of claim 2 wherein each ultrashort electric field pulse has a rise time which is no more than about 20% of its pulse duration.

25. The method of claim 2 wherein each ultrashort electric field pulse has a total energy of a total energy of at least about 10 mJ/cc.

26. The method of claim 25 wherein each ultrashort electric field pulse has a total energy of no more than about 10 J/cc.

27. The method of claim 2 wherein each ultrashort electric field pulse has an amplitude of at least about 20 kV/cm.

28. The method of claim 27 wherein each ultrashort electric field pulse has an amplitude of no more than about 1 MV/cm.

29. The method of claim 2 wherein the target cells are included in a tissue.

30. The method of claim 2 wherein each ultrashort electric field pulse has a pulse duration of about 1 nanosecond to about 500 nanoseconds.

31. The method of claim 2 wherein the target cells are eukaryotic cells.

32. The method of claim 31 wherein the eukaryotic cells include cancer cells.

33. The method of claim 32 wherein the cancer cells are leukemia cells or fibrosarcoma cells.

34. The method of claim 31 wherein the eukaryotic cells include fat cells, bone cells, vascular cells, muscle cells, cartilage cells or a combination thereof.

35. The method of claim 2 wherein each ultrashort electric field pulse has a pulse duration of about 10 to about 300 nanoseconds and a pulse amplitude of about 20 kV/cm to about 500 kV/cm.

36. A method for destroying target cells in a tissue comprising applying to said target cells one or more ultrashort electric field pulses of sufficient amplitude and duration to collectively activate annexin binding on an outer cell surface membrane of said target cells without causing an immediate, irreversible disruption of the outer cell surface membrane in said target cells, whereby destruction of said target cells is initiated;

wherein each ultrashort electric field pulse has a pulse duration of about 10 to about 500 nanoseconds and a pulse amplitude of about 20 kV/cm to about 300 kV/cm.

37. A method for initiating apoptosis in target cells in a tissue comprising applying at least one ultrashort electric field pulse to said target cells, whereby apoptosis is initiated in said target cells;

wherein each ultrashort electric field pulse has a pulse duration of about 10 to about 500 nanoseconds and a pulse amplitude of about 20 kV/cm to about 300 kV/cm.

38. The method of claim 1 wherein each ultrashort electric field pulse is a rectangular pulse or a trapezoidal pulse.

39. The method of claim 1 wherein each ultrashort electric field pulse has a Fourier spectrum which includes frequencies with amplitudes greater than $V_{MAX}/2$ between about 1 MHz and about 1 GHz.

40. The method of claim 1 wherein the ultrashort electric field pulse has a rise time of no more than about 50 nsec.

41. The method of claim 16 wherein each ultrashort electric field pulse has a rise time which is no more than about 20% of its pulse duration.

42. The method of claim 1 wherein each ultrashort electric field pulse has a total energy of a total energy of at least about 10 mJ/cc.

43. The method of claim 42 wherein each ultrashort electric field pulse has a total energy of no more than about 10 J/cc.

44. The method of claim 1 wherein each ultrashort electric field pulse has an amplitude of at least about 20 kV/cm.

45. The method of claim 44 wherein each ultrashort electric field pulse has an amplitude of no more than about 1 MV/cm.

46. The method of claim 1 wherein the target cells are included in a tissue.

47. The method of claim 1 wherein each ultrashort electric field pulse has a pulse duration of about 1 nanosecond to about 500 nanoseconds.

48. The method of claim 1 wherein said target cells include cancer cells.

49. The method of claim 48 wherein the cancer cells are leukemia cells or fibrosarcoma cells.

50. The method of claim 1 wherein said target cells include fat cells, bone cells, vascular cells, muscle cells, cartilage cells or a combination thereof.

51. The method of claim 1 wherein each ultrashort electric field pulse has a pulse duration of about 10 to about 300 nanoseconds and a pulse amplitude of about 20 kV/cm to about 500 kV/cm.

52. The method of claim 1 comprising applying 3 to about 20 of the ultrashort electric field pulses to the target cells.

* * * * *

UNITED STATES PATENT AND TRADEMARK OFFICE
CERTIFICATE OF CORRECTION

PATENT NO.    : 6,326,177 B1
DATED         : December 4, 2001
INVENTOR(S)   : Karl H. Schoenbach, Stephen J. Beebe and E. Stephen Buescher It is certified that error appears in the above-identified patent and that said Letters Patent is hereby corrected as shown below:

<u>Column 21,</u>
Lines 66 and 67, delete the second occurrence of the following phrase "wherein each ultrashort electric field pulse has".

Signed and Sealed this

Fourth Day of June, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,326,177 B1
DATED : December 4, 2001
INVENTOR(S) : Karl H. Schoenbach, Stephen J. Beebe and Stephen E. Buescher It is certified that error appears in the above-identified patent and that said Letters Patent is hereby corrected as shown below:

Title page,
Item [73], Assignees, "Old Dominion University" should be -- Old Dominion University Research Foundation --.

Signed and Sealed this

Third Day of January, 2006

JON W. DUDAS
*Director of the United States Patent and Trademark Office*